United States Patent
Thompson et al.

(10) Patent No.: US 11,459,320 B2
(45) Date of Patent: Oct. 4, 2022

(54) DEUTERATED ALPHA5 SUBUNIT-SELECTIVE NEGATIVE ALLOSTERIC MODULATORS OF GAMMA-AMINOBUTYRIC ACID TYPE A RECEPTORS AS FAST ACTING TREATMENT FOR DEPRESSION AND MOOD DISORDERS

(71) Applicants: UNIVERSITY OF MARYLAND, BALTIMORE, Baltimore, MD (US); THE UNITED STATES OF AMERICA, AS REPRESENTED BY THE SECRETARY, DEPARTMENT OF HEALTH AND HUMAN SERVICES, Bethesda, MD (US)

(72) Inventors: Scott Thompson, Baltimore, MD (US); Adam Van Dyke, Baltimore, MD (US); Craig Thomas, Gaithersburg, MD (US); Patrick Morris, Laurel, MD (US)

(73) Assignees: UNIVERSITY OF MARYLAND, BALTIMORE, Baltimore, MD (US); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 16/642,445

(22) PCT Filed: Aug. 28, 2018

(86) PCT No.: PCT/US2018/048339
§ 371 (c)(1),
(2) Date: Feb. 27, 2020

(87) PCT Pub. No.: WO2019/046300
PCT Pub. Date: Mar. 7, 2019

(65) Prior Publication Data
US 2020/0199119 A1   Jun. 25, 2020

Related U.S. Application Data

(60) Provisional application No. 62/550,826, filed on Aug. 28, 2017.

(51) Int. Cl.
| | |
|---|---|
| C07D 417/14 | (2006.01) |
| A61P 25/24 | (2006.01) |
| C07D 261/08 | (2006.01) |
| C07D 413/12 | (2006.01) |
| A61K 9/19 | (2006.01) |
| A61K 45/06 | (2006.01) |

(52) U.S. Cl.
CPC ............ C07D 417/14 (2013.01); A61P 25/24 (2018.01); C07D 261/08 (2013.01); C07D 413/12 (2013.01); A61K 9/19 (2013.01); A61K 45/06 (2013.01); C07B 2200/05 (2013.01)

(58) Field of Classification Search
CPC .... C07D 417/14; C07B 2200/05; A61P 25/24
See application file for complete search history.

(56) References Cited

U.S. PATENT DOCUMENTS 10,421,730 B2 * 9/2019 Blomgren ............... C07C 25/13
2016/0354315 A1   12/2016 Li

FOREIGN PATENT DOCUMENTS

| WO | 2009/071476 A1 | 6/2009 |
| WO | 2015/153658 | 10/2015 |
| WO | 2019/046300 | 3/2019 |

OTHER PUBLICATIONS

Fischell et al., Rapid Antidepressant Action and Restoration of Excitatory Synaptic Strength After Chronic Stress by Negative Modulators of Alpha5-Containing GABAA Receptors, Neuropsychopharmacology, 2015, pp. 2499-2509, vol. 40.
Zanos et al., MDAR inhibition-independent antidepressant actions of ketamine metabolites, Nature, 2016, pp. 481-486, vol. 533.
European Search Report for Patent Application No. 18852438.3 dated Apr. 6, 2021, pp. 1-7.
Froestl et a l., Cognitive Enhancers (Nootropics). Part 1: Drugs Interacting with Receptors, Journal of Alzheimer's Disease, vol. 32, 2012, pp. 793-887.
Jahan et al., Optimization of Substituted Imidazobenzodiazepines as Novel Asthma Treatments, HHS Public Access, PMC, Author manuscript, Jan. 27, 2018.
International Search Report and Written Opinion for International Patent Application No. PCT/US2018/048339 dated Oct. 17, 2018, pp. 1-6.
John R. Atack, et al.; "In Vitro and in Vivo Properties of 3-tert-Butyl-7-(5-methylisoxazol-3-yl)-2-(1-methyl-1H-1,2,4-triazol-5-ylmethoxy)-pyrazolo[1,5-d]-[1,2,4]triazine (MRK-016), a GABAA Receptor 5 Subtype-Selective Inverse Agonist"; The Journal of Pharmacology and Experimental Therapeutics vol. 331, No. 2; 2009; pp. 470-484.
Rajwana Jahan, et al.; "Optimization of Substituted Imidazobenzodiazepines as Novel Asthma Treatments"; Eur J Med Chem. Jan. 2, 20177; 126: pp. 550-560.

(Continued)

*Primary Examiner* — Kamal A Saeed
(74) *Attorney, Agent, or Firm* — Wolter Van Dyke Davis, PLLC; Eugene Molinelli; Martha Cassidy

(57) ABSTRACT

The present invention relates to novel alpha5 subunit-selective negative allosteric modulators of GABA$_A$ receptors that have been deuterated to improve their medicinal properties by prolonging their half-lives, rendering them useful as fast-acting pharmaceutical treatments for depression related disorders.

6 Claims, 14 Drawing Sheets

(56) References Cited

OTHER PUBLICATIONS

Theresa M. Ballard, et al.; "RO4938581, a novel cognitive enhancer acting at GABAA α5 subunit-containing receptors"; Psychopharmacology (2009); pp. 207-223.

Uwe Rudolph, et al.; "GABAA Receptor Subtypes: Therapeutic Potential in Down Syndrome, Affective Disorders, Schizophrenia, and Autism" Annu. Rev. Pharmacol. Toxicol. 2014; vol. 54; pp. 483-507.

Federico Bolognani, et al.; "RG1662, a Selective GABAA α5 ReceptorNegative Allosteric Modulator, IncreasesGamma Power in Young Adults with DownSyndrome"; AAN Publications; https://n.neurology.org/content/84/14_Supplement/P6.273. Abstract only.

\* cited by examiner

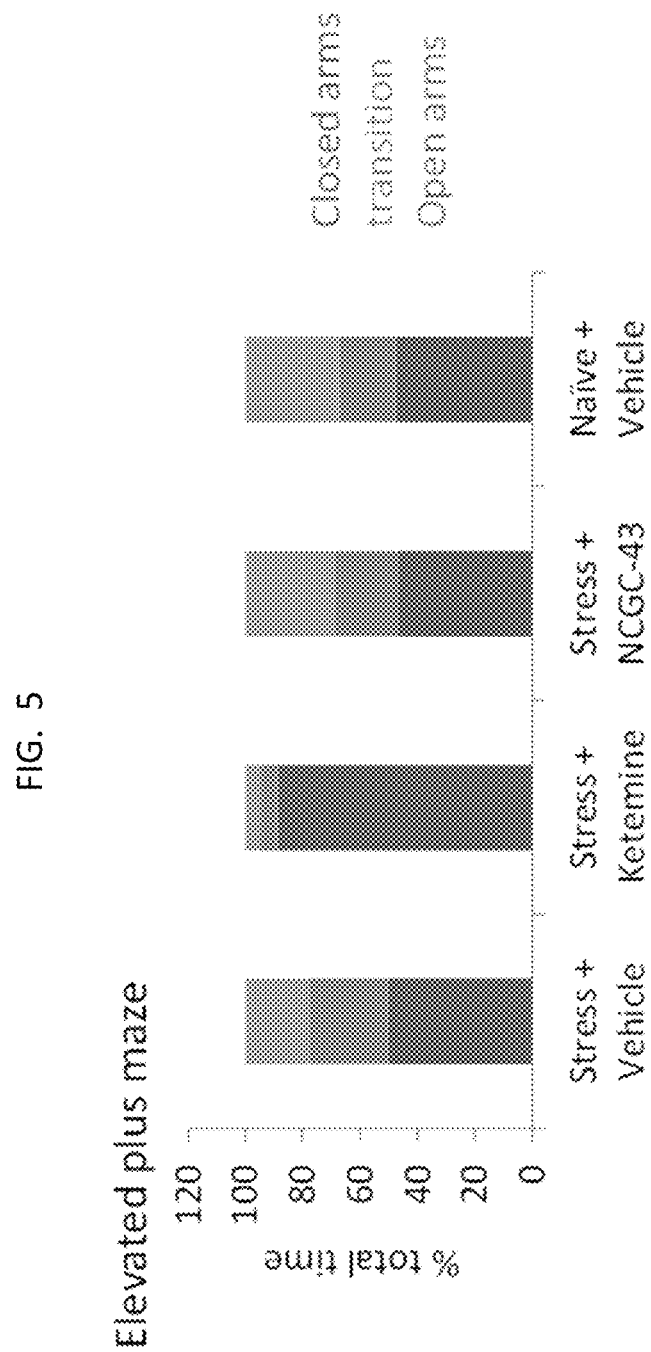

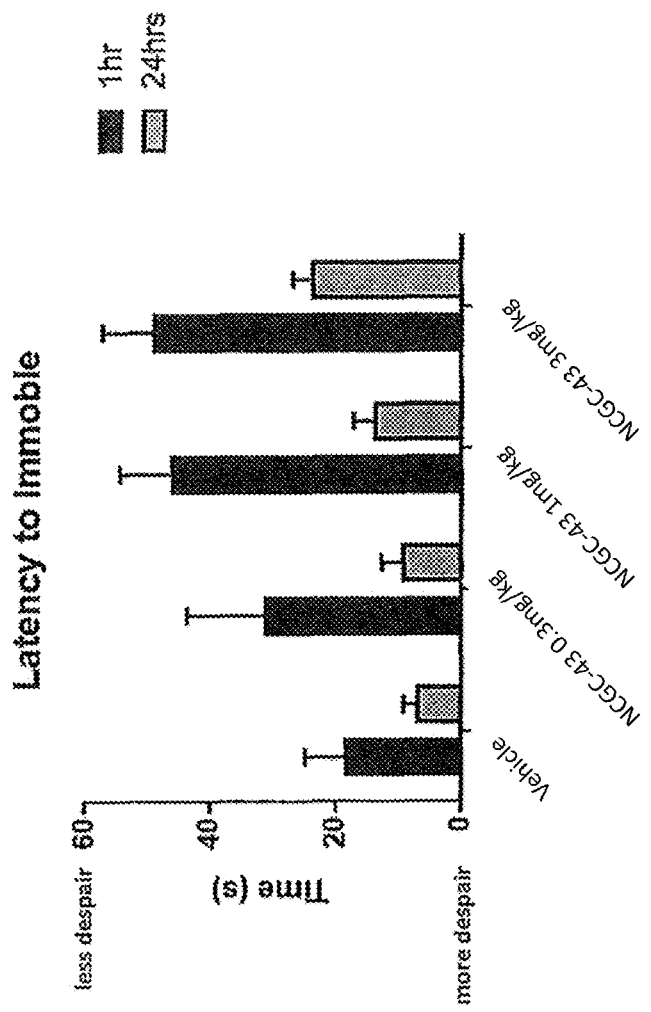

DEUTERATED ALPHA5 SUBUNIT-SELECTIVE NEGATIVE ALLOSTERIC MODULATORS OF GAMMA-AMINOBUTYRIC ACID TYPE A RECEPTORS AS FAST ACTING TREATMENT FOR DEPRESSION AND MOOD DISORDERS

CROSS-REFERENCE TO RELATED APPLICATIONS

This application is a 371 national stage application of PCT Application No. PCT/US18/48339, filed Aug. 28, 2018, and claims the benefit of U.S. provisional application Ser. No. 62/550,826, filed 28 Aug. 2017. The entire contents of these applications are hereby incorporated by reference as if fully set forth herein.

GOVERNMENT FUNDING SUPPORT

This invention was made with government support under grant no. MH086828 awarded by the National Institutes of Health. The government has certain rights in the invention.

BACKGROUND

1. Field of the Invention

The present invention relates to the fields of neurology, psychiatry, pharmacology and medicine. Specifically, the invention relates to compositions and methods for treating, preventing or ameliorating depression and/or other psychiatric and neurological conditions using negative allosteric modulators (NAM) selective for gamma-aminobutyric acid (GABA) receptors containing alpha5 subunits that have been deuterated at key positions to enhance their medicinal value as fast-acting antidepressant compounds. The deuterated compounds have enhanced properties because the deuteration has been performed specifically to prolong their half-life in the human body.

2. Background of the Invention

The gamma-aminobutyric acid A receptor ($GABA_AR$) is an ionotropic receptor and ligand gated ion channel. $GABA_ARs$ are found in all organisms with a central nervous system. Because of their wide distribution within the nervous system of mammals, they play a role in virtually all brain functions. The endogenous ligand of the $GABA_AR$ is gamma-aminobutyric acid (GABA), the major inhibitory neurotransmitter in the central nervous system. $GABA_ARs$ are heteropentameric, ligand-gated ion channels. Nineteen $GABA_A$ receptor subunits have been identified to date. Most $GAB_AA$ receptors contain $\alpha$, $\beta$, and $\gamma2$ subunits in a 2:2:1 stoichiometry. The primary activation site of the $GABA_AR$ is the binding site for GABA and for several drugs, including muscimol, gaboxadol, and bicuculline. The interface between adjacent $\gamma2$ and a subunits form the benzodiazepine site, an allosteric modulator of channel gating. The identity of the $\alpha$ subunit determines the pharmacological profile of this site. Receptors containing $\alpha1$, $\alpha2$, or $\alpha3$ subunits are potentiated by zolpidem, a benzodiazepine type 1 agonist, whereas receptors containing $\alpha5$ subunits are essentially insensitive to zolpidem. Drugs binding at this site can affect the ability of GABA to activate the $GABA_AR$, including positive allosteric modulators that promote function and negative allosteric modulators that decrease function.

Recent studies have shown that a1 subunits mediate the sedative, anticonvulsant and amnestic effects of benzodiazepines preferentially, whereas the $\alpha2$ and $\alpha3$ subunits mediate their anxiolytic effects. In addition to the anxiolytic agonists of benzodiazepines, there is a class of drugs, exemplified by the $\beta$-carbolines that act as full or partial inverse agonists at the benzodiazepine site to decrease $GABA_A$ receptor function. Partial inverse agonists offer the advantage of a wider therapeutic concentration range and a lower likelihood of producing anxiety or epileptiform discharge, in specific embodiments of the disclosure.

$\alpha5$-subunit mRNA is highly expressed in the pyramidal cells of the hippocampus and cortex (Allen Brain Atlas) and $\alpha5$-containing $GABA_A$ receptors are localized in the dendrites of hippocampal CA1 pyramidal cells at synaptic and extrasynaptic sites. Because disinhibition promotes induction of long-term potentiation (LTP), and because of their selective forebrain localization, drugs that selectively inhibit $\alpha5$-containing receptors are being developed as cognitive enhancers. It has been shown, for example, that partial inverse agonists of $\alpha5$-containing $GABA_A$ receptors enhance associative memory acquisition in hippocampal-dependent learning tasks.

The antidepressant-like efficacy of partial inverse agonists of $\alpha5$ subunit-containing $GABA_A$ receptors in animal models of depression-like behavior was first shown by Fishell et al (2015). Rapid onset of antidepressant action, shown using established preclinical models, for example, is highly desirable from a clinical perspective and has never been attempted with these compounds. The studies allow one to demonstrate that partial inverse agonists of $\alpha5$ subunit-containing $GABA_A$ receptors are useful at least as a treatment for depression.

Depressive disorders and their sequelae, such as suicide, are a serious problem worldwide. The current gold standard therapy for depression, selective serotonin reuptake inhibitors (SSR1s), usually must be administered for over 6-8 weeks to eventually reach efficacy and are effective in only about 50% of patients that use them. There are no fast acting antidepressants currently approved by the FDA. Those currently under development display a number of side effects that limit their clinical utility, such as liability for abuse and tendency to induce psychosis-like responses. Alternative medications for depression do exist, however many of these suffer from the same need for prolonged treatment before efficacy, and many of these also are ineffective or only partially effective. Therefore, there is a need to identify new drugs that can be used to treat depressive disorders and reduce the incidence of suicide on a worldwide basis.

The gamma-aminobutyric acid A receptor ($GABA_AR$) is an ionotropic receptor and ligand gated ion channel. Its endogenous ligand is gamma-aminobutyric acid (GABA), the major inhibitory neurotransmitter in the central nervous system. The primary activation site of the $GABA_AR$ is the binding site for GABA and for several drugs, including muscimol, gaboxadol, and bicuculline. A second binding site on $GABA_AR$ is the so-called benzodiazepine receptor site. Drugs binding at this site can affect (promote or impair) the ability of GABA to activate the $GABA_AR$. $GABA_ARs$ are found in all organisms with a central nervous system. Because of their wide distribution within the nervous system of mammals, they play a role in virtually all brain functions.

SUMMARY OF THE INVENTION

The present invention relates to compositions and methods for the treatment of certain medical conditions, including depression-related disorders; anxiety-related disorders; attention-related disorders; psychosis-related disorders; personality disorders; eating disorders; cognitive impairment (including that which follows traumatic brain injury (TBI) or non-TBI-related cognitive impairment; neuropathic pain; chronic muscle or bone pain; diabetic complications resulting in nerve injury; generalized attack of muscular weakness; recurring sleep episodes during the day; migraine; addiction; or a combination thereof.

Specifically, the invention comprises a deuterated $GABA_{A5}$-NAM compound according to Formula I:

Formula I

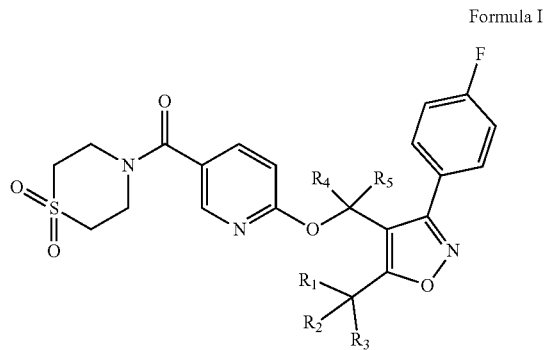

wherein $R_1$, $R_2$, and $R_3$ each independently are H or D, with the proviso that at least one of $R_1$, $R_2$ and $R_3$ is D, and wherein $R_4$ and $R_5$ each independently are H or D.

In some embodiments, the invention relates to a $GABA_{A5}$-NAM compound selected from the group consisting of: ethyl (S)-7-methoxy-9-oxo-11,12,13,13a-tetrahydro-9H-benzo[e]imidazo[5,1-c]pyrrolo[1,2-a][1,4]diazepine-1-carboxylate (L-655,708); 3-bromo-10-(difluoromethyl)-9H-benzo[f]imidazo[1,5-a][1,2,4]triazolo[1,5-d][1,4]diazepine (RO4938581); N-benzyl-6-ethoxy-4-oxo-1H-1,5-naphthyridine-3-carboxamide (CP-457,920); 3-tert-Butyl-7-(5-methylisoxazol-3-yl)-2-(1-methyl-1H-1,2,4-triazol-5-yl-methoxy)pyrazolo(1,5-d)(1,2,4)triazine (MRK-016); and (1,1-dioxidothiomorpholino)(6-((3-(4-fluorophenyl)-5-methylisoxazol-4-yl)methoxy)pyridin-3-yl)methanone (RG-1662); which is deuterated. In other embodiments, the invention relates to a compound selected from the group consisting of (3-(4-fluophenyl)-5-(methyl-d3)isoxazol-4yl)methanol; 6-((3-(4-fluorophenyl)-5-(methyl-d3)isoxazol-4yl)methoxy)nicotinonitrile; and 6-((3-(4-fluorophenyl)-5-(methyl-d3)isoxazol-4-yemethoxy)nicotinic acid.

Preferably, the deuterated $GABA_{A5}$-NAM compound is according to Formula II

Formula II

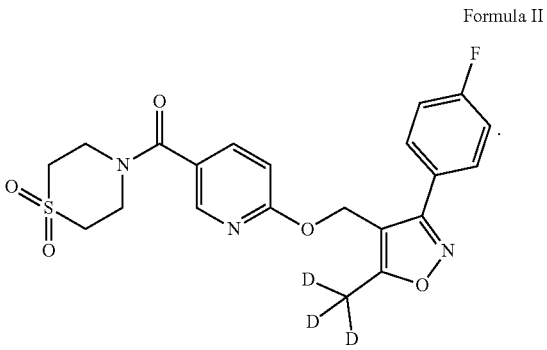 [SMILES: [2H]C([2H])([2H])c1onc(-c2ccc(F)cc2)c1COc1ccc(C(=O)N2CCS(=O)(=O)CC2)cn1]

In some embodiments, the invention also comprises a deuterated Basmisanil-related or Basmisanil-derivative compound as discussed herein, which is synthesized by: (a) treating (3-(4-fluorophenyl)-5-methylisoxazol-4-yl)methanol with a base or under basic conditions in the presence of a deuterium donor or followed by a deuterium donor; (b) adding the product of step (a) to 6-chloronicotinonitrile or methyl 6-chloronicotinate; (c) hydrolyzing the product of step (b) to the carboxylic acid; and (d) amide coupling the product of step (c) with thiomorpholine 1,1-dioxide or a salt there. The deuterium donor can be $D_2O$ or $CD_3OD$.

In additional embodiments, the invention relates to a method of forming a deuterated RG-1662 compound comprising treating a compound selected from the group consisting of 6-((3-(4-fluorophenyl)-5-methylisoxazol-4-yl)methoxy)nicotinonitrile; 6-((3-(4-fluorophenyl)-5-methylisoxazol-4-yl)methoxy)nicotinamide; and 6-((3-(4-fluorophenyl)-5-methylisoxazol-4-yl)methoxy)nicotinic acid, with base in the presence of a deuterium-containing solvent. Preferably, the deuterium-containing solvent is $D_2O$.

Certain embodiments of the invention relate to a deuterated $GABA_{A5}$-NAM compound of claim 1 which has a longer biological half-life when administered to a mammal than a non-deuterated compound of the same structure.

The invention also relates, in certain embodiments, to a method of treating a depression-related disorder in a human subject in need thereof, comprising administering a therapeutically effective amount of a deuterated $GABA_{A5}$-NAM compound as described herein to the subject. In this method, the deuterated $GABA_{A5}$-NAM compound can be administered orally, intradermally, intramuscularly, intraperitoneally, intravenously, via insufflation, or in a dermal patch, and can be administered to the subject every 0.5, 1, 2, 3 or 4 days.

In some embodiments the method involves those wherein the deuterated $GABA_{A5}$-NAM compound is administered to the subject in combination with one or more additional therapies for the treatment or amelioration of depression. These therapies can include, but are not limited to administration of an antidepressant drug selected from the group consisting of a monoamine oxidase inhibitor, a selective serotonin reuptake inhibitor, a serotonin-norepinephrine reuptake inhibitor, a triple reuptake inhibitor, a modulator of CNS acetylcholine function, a stimulant, an anti-glucocorticoids, an NMDA-type glutamate receptor antagonist, a tricylic antidepressants, and any combination thereof. The depression-related disorder can be selected from one or more of general depression, major depressive disorder (clinical depression), dysthymia, suicidality, unipolar depression, bipolar depression, psychotic depression, atypical depression, seasonal affective disorder, premenstrual dysphoric disorder, endogenous depression, catatonic depression, post-traumatic stress disorder, postpartum depression, depression arising from illness or injury, depression arising from drugs or alcohol, treatment-resistant depression, and any combination thereof. Other disorders and conditions included in the definition of depression-related disorders are those in with these symptoms occur as a secondary consequence of some other primary medical condition, such as a tumor, trauma, substance abuse disorder, alcoholism. In preferred methods, the deuterated $GABA_{A5}$-NAM compound is selected from the group consisting of (3-(4-fluophenyl)-5-(methyl-d3)isoxazol-4yl) methanol; 6-((3-(4-fluorophenyl)-5-(methyl-d3)isoxazol-4yl-methoxy)nicotinonitrile; 6-((3-(4-fluorophenyl)-5-(methyl-d3)isoxazol-4-yl-methoxy)nicotinic acid; and (1,1- dioxidothiomorpholino)(6-((3-(4-fluorophenyl)-5-(methyl-d3)isoxazol-4-yl-methoxy)pyridine-3-yl)methadone. Also, in preferred methods, the subject is a human.

DESCRIPTION OF THE FIGURES

FIG. 5 is a graph showing results of the elevated plus maze test as indicated.

FIG. 7 is a graph showing the dose-response relationship of NCGC-43 in the forced swim test.

DETAILED DESCRIPTION

1. Definitions

Figure 1A:
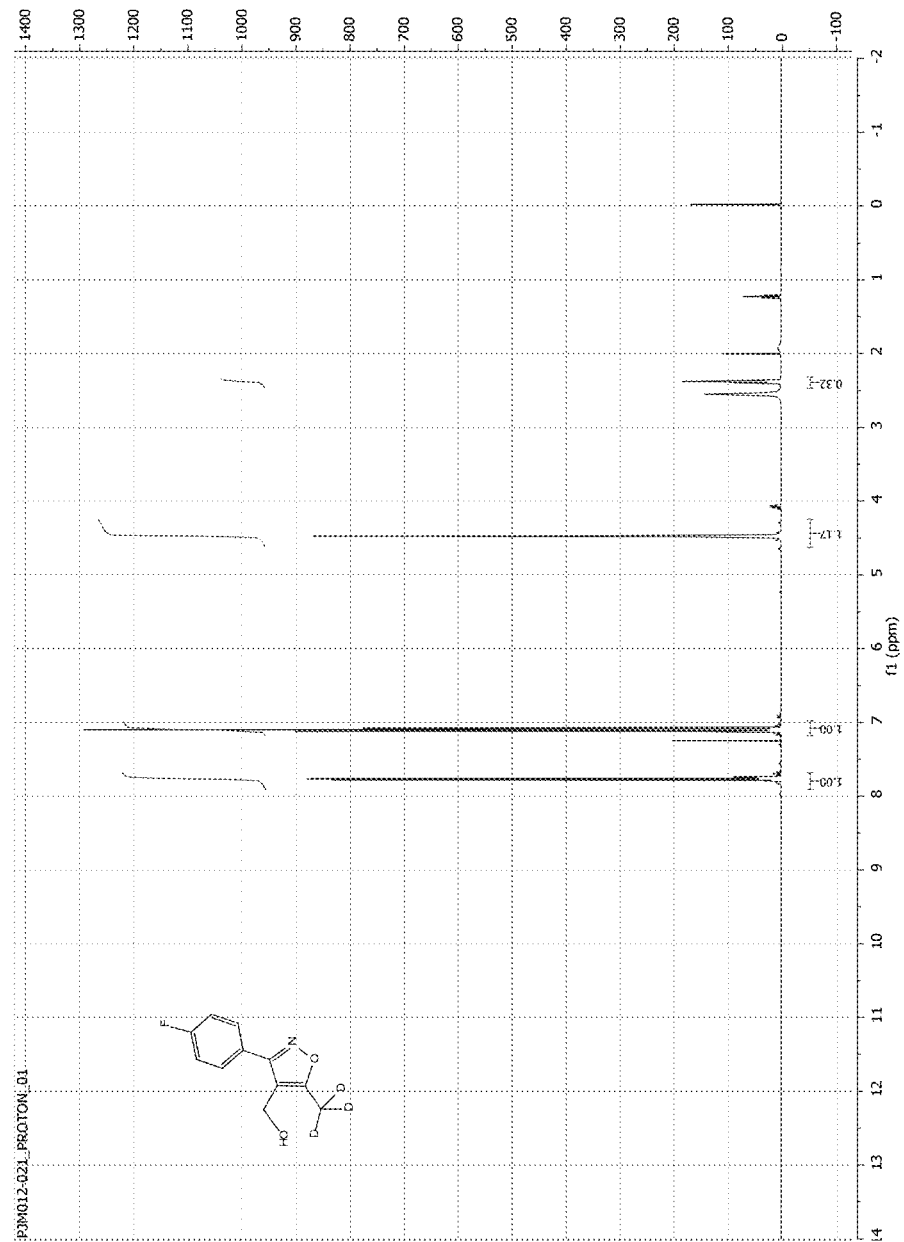
FIG. 1A, FIG. 1B, FIG. 1C, FIG. 1D, FIG. 1E, and FIG. 1F show NMR spectrometry results confirming the chemical identity of intermediate compounds as indicated by structure, and the final product of the synthetic scheme for generating NCGC-43, as shown in Example 1, below.
Figure 1B:
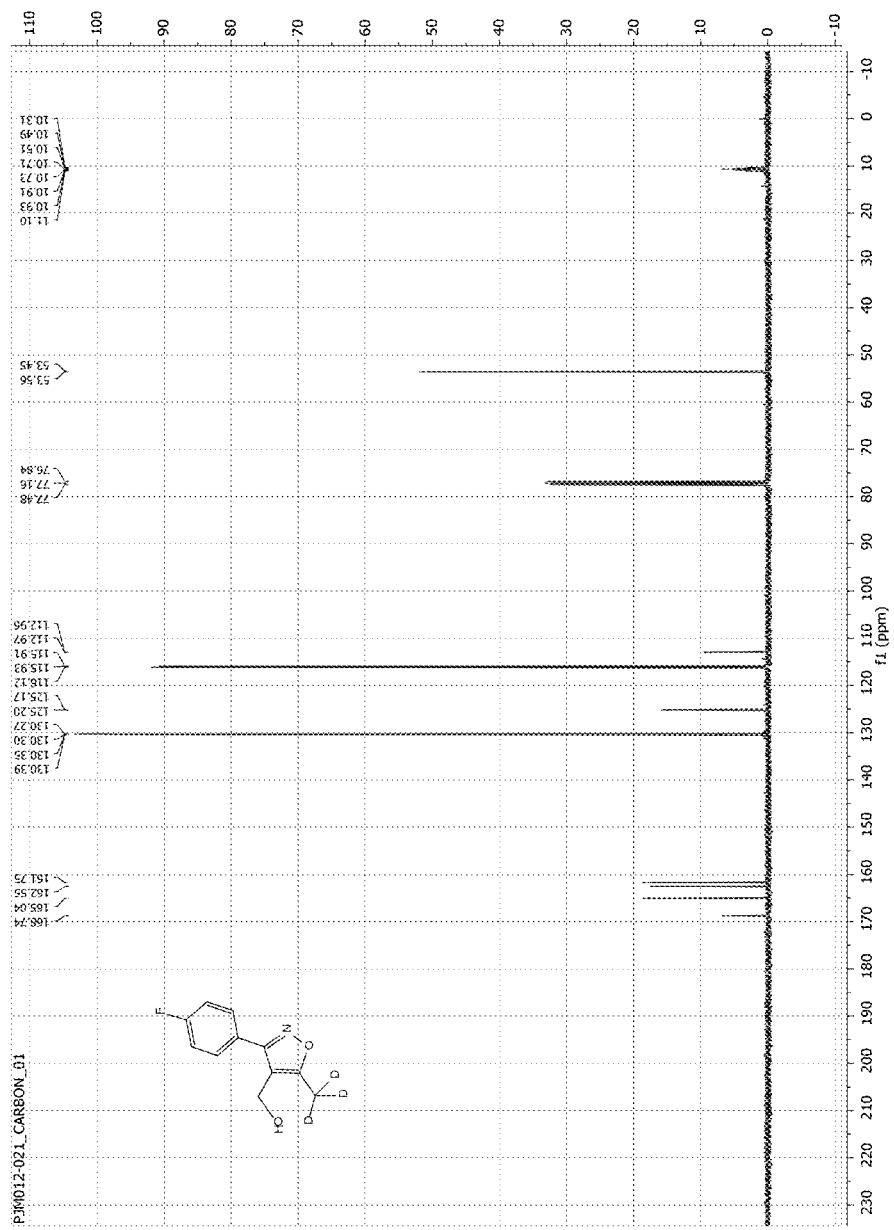
Figure 1C:
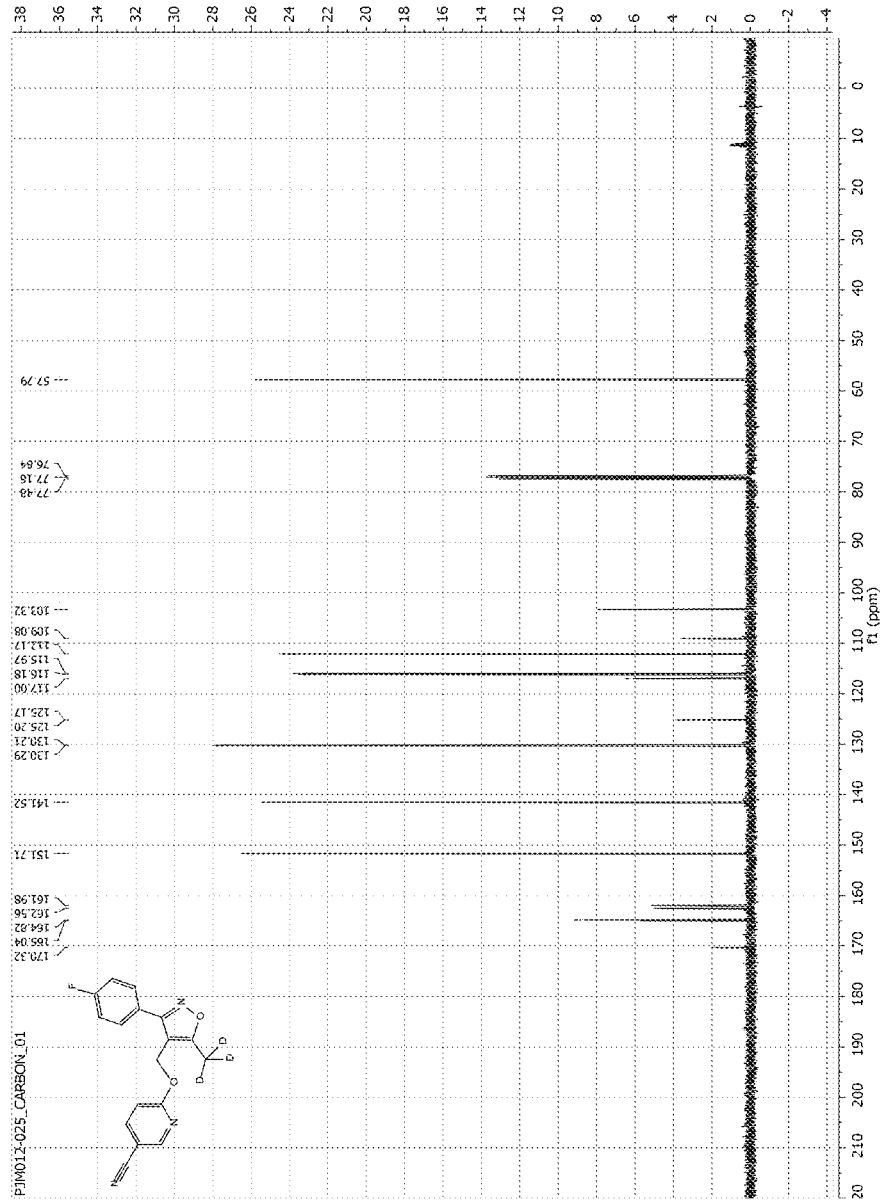
Figure 1D:
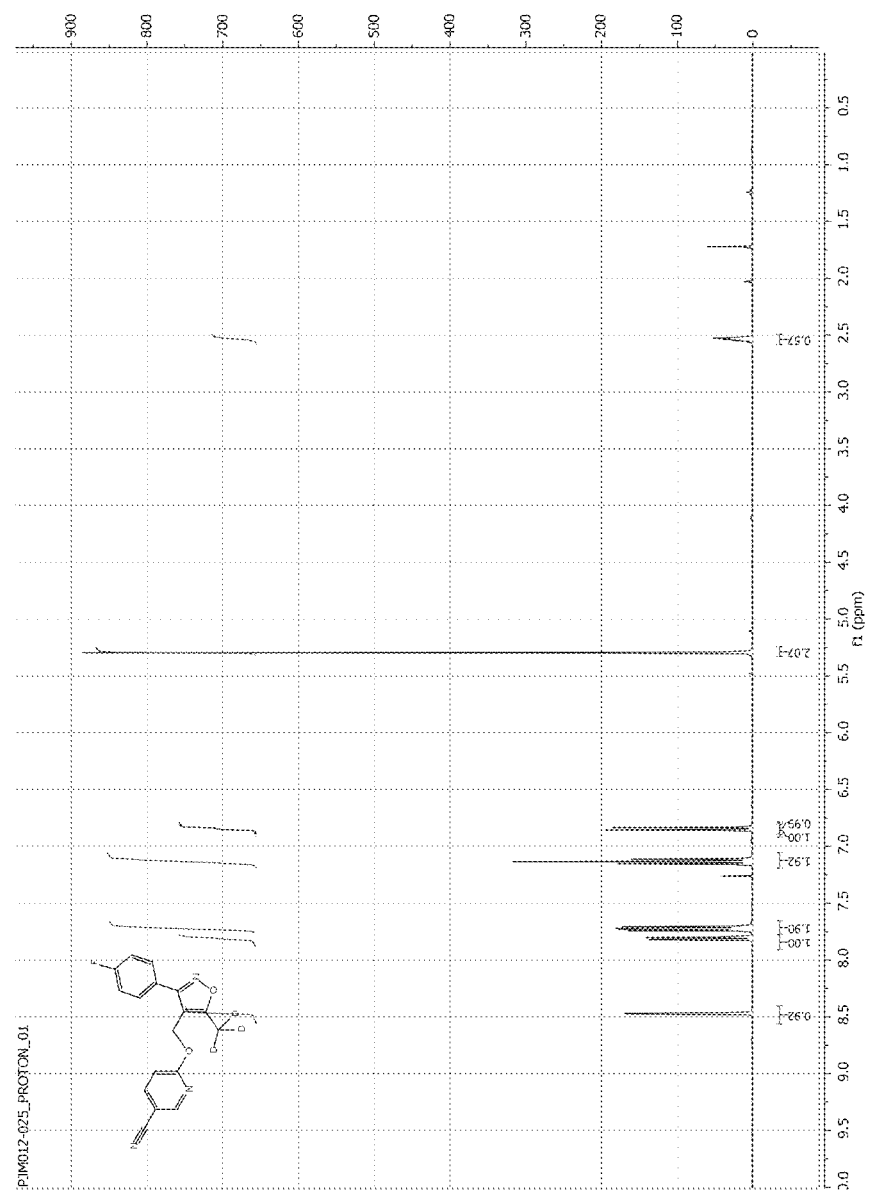
Figure 1E:
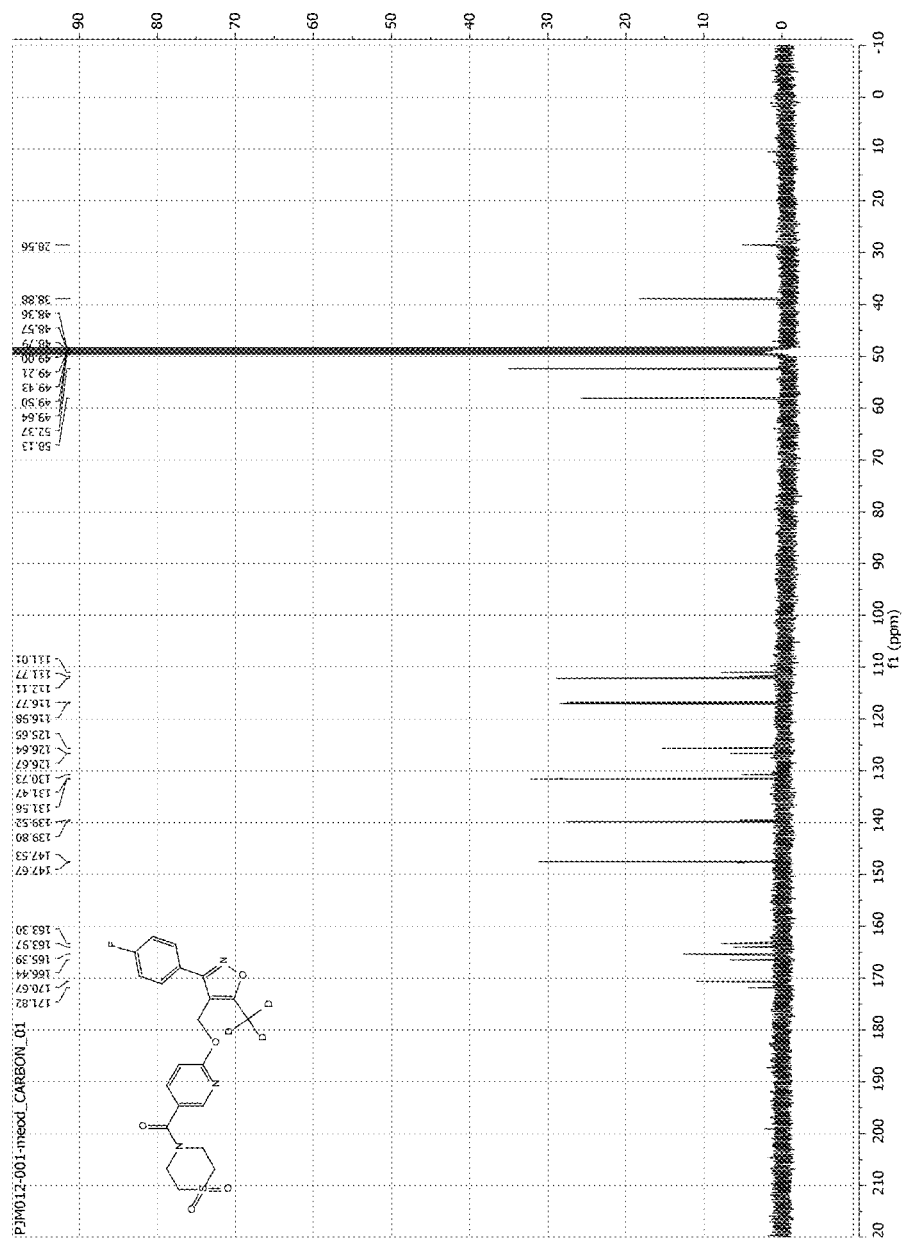
Figure 1F:
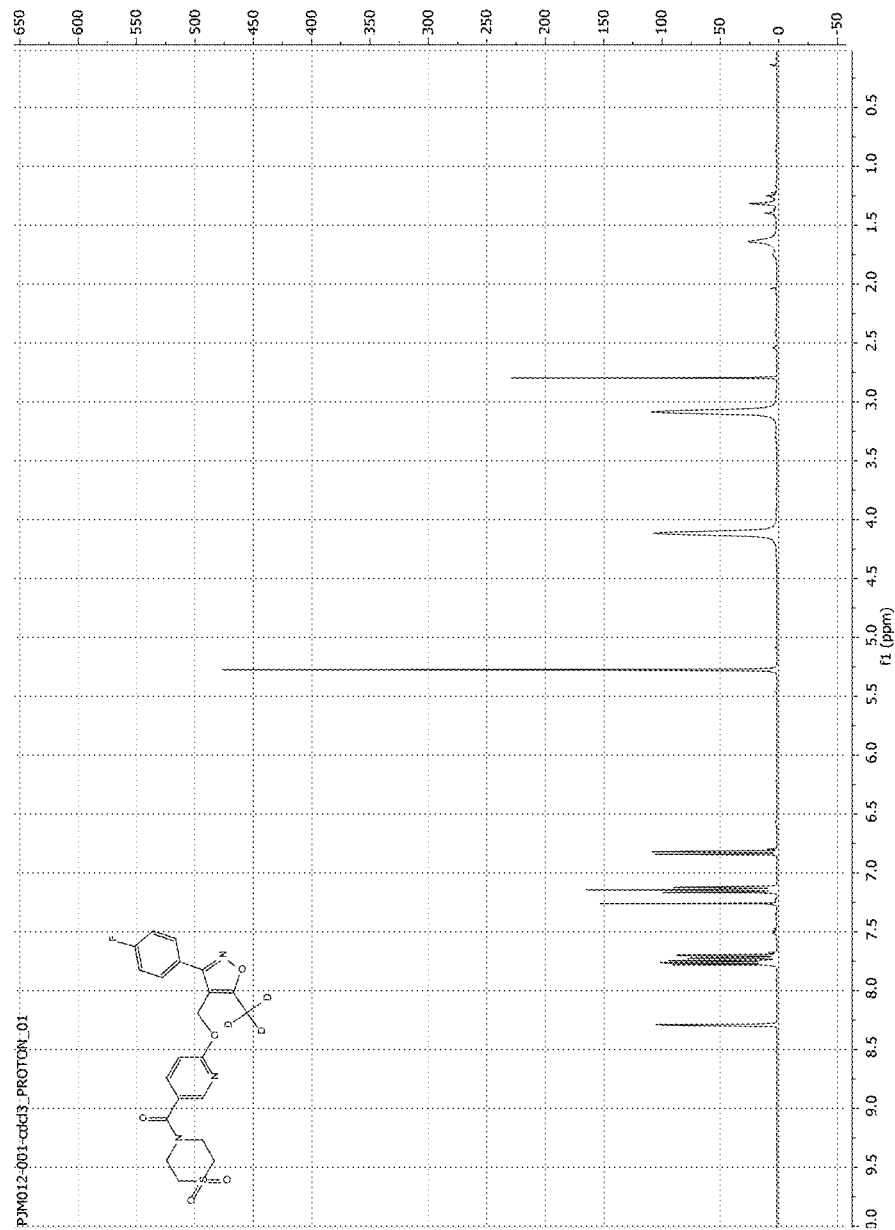

Unless defined otherwise, all technical and scientific terms used herein have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

The term "about," as used herein, means plus or minus 20 percent of the recited value, so that, for example, "about 0.125" means 0.125±0.025, and "about 1.0" means 1.0±0.2.

The term "deuterium," as used herein, refers to a stable isotope of hydrogen with a mass approximately twice of the most common isotope, i.e., a mass of about 2 atomic mass units.

The term "biological half-life," as used herein, refers to the time that a living body requires to remove one half the quantity of an administered substance through normal elimination.

The term "treating" refers to an intervention in disease such as administration of a pharmaceutical composition to a subject in need. Such treatment involves taking a step to obtain beneficial or desired results, including clinical results such as mitigating, alleviating or ameliorating one or more symptoms of a disease, disorder, or condition; diminishing the extent of the disease, disorder, or condition; delaying or slowing the progression of a disease, disorder, or condition; preventing or reducing the chance or frequency of recurrence of a disease, disorder, or condition; ameliorating or stabilizing a metric (statistic) of the disease, disorder, or condition; or promoting by direct or indirect means the efficacy of another medication with benefit in treating the disease, disorder, or condition.

The term "depression-related disorder," as used herein, includes any disorder causing, related to or defined by depression and any disorder or condition having depressive symptoms. As used herein, this term also includes cognitive, memory, substance abuse, and psychotic disorders. Depressive disorders include, but are not limited to general depression, major depressive disorder (clinical depression), dysthymia, suicidality, unipolar depression, bipolar depression, psychotic depression, atypical depression, seasonal affective disorder, premenstrual dysphoric disorder, endogenous depression, catatonic depression, post-traumatic stress disorder, postpartum depression, and any combination thereof. Other disorders and conditions included in the definition of depression-related disorders are anxiety-related disorders; anhedonia; attention-related disorders; psychosis-related disorders; personality disorders; sleep disorders; eating disorders; cognitive impairment (including that which follows traumatic brain injury (TBI) or non-TBI-related cognitive impairment; memory impairment; disorders of learning; neuropathic pain; chronic muscle or bone pain; diabetic neuropathy; generalized attack of muscular weakness; recurring sleep episodes during the day; migraine; addiction; or a combination thereof. Other disorders and conditions included in the definition of depression-related disorders are those in with these symptoms occur as a secondary consequence of some other primary medical condition, such as a tumor, substance abuse disorder, alcoholism.

The term "subject in need," as used herein, refers to any animal, preferably a mammal, and most preferably a human. Laboratory animals, companion and service animals, farm animals, and zoo animals are included in this definition. Preferred animals include mice, rats, rabbits, monkeys, apes, and humans.

The term "therapeutically effective amount," as used herein, means an amount of a therapeutic agent, which, when administered to a subject, has the intended therapeutic effect. A therapeutic effect is an effect that treats the intended disorder or condition, including improving the disease, disorder or condition, or a symptom thereof, including reduction of a symptom or delaying the onset or reoccurrence of the disease, disorder, condition, or symptom. The full therapeutic effect does not necessarily occur by administration of one dose and may occur only after administration of a series of doses. Thus, a therapeutically effective amount may be administered in one or more administrations.

2. Overview

In specific embodiments, the medical condition is a depression-related disorder; an anxiety-related disorder; an attention-related disorder; a psychosis-related disorder; a personality disorder; an eating disorder; cognitive impairment (including that which follows traumatic brain injury (TBI) or non-TBI-related cognitive impairment; neuropathic pain; chronic muscle or bone pain; diabetic complications resulting in nerve injury; generalized attack of muscular weakness; recurring sleep episodes during the day; migraine; addiction; alcoholism; substance use disorder; or any combination thereof. Specifically, the invention relates to fast-acting deuterated antidepressant compositions that can act as negative allosteric modulators of alpha5 subunit-containing $GABA_A R$.

3. Embodiments of the Invention

A. General Comments

Embodiments of the invention concern compositions and methods for the treatment of one or more medical conditions, in particular including depression and similar conditions. The condition may be of any kind, but in specific embodiments the condition being treated is major depression (major depressive disorder) and/or suicidality. Using the inventive compositions and methods, treatment of the medical condition preferably occurs at a more rapid rate than currently known treatments for this type of illness, successfully treats a larger fraction of the patient population, and has fewer deleterious side effects.

In particular embodiments of the disclosure one or more partial inverse agonists of the benzodiazepine binding site of $GABA_A$ receptors containing an α5 subunit produce a rapid antidepressant action in unipolar and bipolar forms of depression and reduce suicidal ideation by restoring the normal function of excitatory synapses. Such considerations may be characterized, by example, using rodent models of depression with face, construct, and predictive validity, such chronic unpredictable stress (CUS) or chronic multimodal stress (restraint, strobe light, and white noise), to characterize the actions of acute administration (24 hours) of α5-selective GABA-NAMs. Antidepressant efficacy of partial inverse agonists of α5 subunit-containing $GABA_A$ receptors can be tested in vivo in laboratory animals, such as mice and rats, using the sucrose preference and social exploration tests (Amat et al., 2010), for example. One could also determine the ability of partial inverse agonists of α5 subunit-containing $GABA_A$ receptors to reverse the electrophysiological correlates of stress-induced depression using electrophysiological and biochemical analyses in vitro. These effects in animal models can be compared with ketamine, a glutamate receptor blocker that is known to have fast antidepressant efficacy in humans (Zarate et al., 2006).

In certain embodiments of this disclosure, patients may undergo standard psychiatric screening for DSM-IV criteria for major depressive episodes. In specific embodiments, a saline solution comprising one or more of the agonists are provided to the individual, such as infused slowly (ca. 30-60 min), for example. Depression-related and other rating tests, such as the Hamilton Depression Rating Scale, Beck Depression Inventory, Visual Analog Scales score for intoxication "high", and the Brief Psychiatric Rating Scale, may be given repeatedly; as an example only, they may be given over a four hour period after drug administration, and daily over the following seven days. Antidepressant efficacy, as well as psychomimetic or anxiogenic responses, is determined upon changes in the test scores, in specific embodiments to show efficacy with a particular compound.

Specific embodiments of the invention involve negative allosteric modulators of alpha5 subunit-containing $GABA_A Rs$, which are fast-acting antidepressants that address depression and/or reduce suicidality. Preferably, these modulators are novel deuterated compounds that offer discreet advantages over the non-deuterated modulators. These advantages can include prolonged bioavailability in the treated subject.

Deuterium is a naturally occurring, stable, non-radioactive isotope of hydrogen. Hydrogen consists of one electron surrounding a nucleus composed of one proton and has a mass of approximately 1.0 atomic mass unit (AMU). Deuterium also has a single electron but its nucleus contains one neutron and one proton, resulting in an atomic mass of approximately 2.0 AMU. When excess deuterium is incorporated into molecules in place of hydrogen, referred to as deuteration, the deuterated compound is similar to the all-hydrogen compound. In general, deuterated compounds have shapes and sizes that are essentially indistinguishable from their all-hydrogen analogues. Moreover, deuterium has remarkably low systemic toxicology. Single celled organisms can often be grown in conditions of full deuteration. In addition, humans can tolerate high levels of deuterium in body fluids. Additionally, deuterated compounds have a long history of safe use in humans as metabolic and pharmacokinetic probes. Selective deuteration can thus be used in pharmaceutical compounds and compositions to create new drugs, as herein described, that meet unmet medical needs. Several deuterated drugs have entered into clinical evaluation. The first deuterated drug has been approved by the FDA (Austedo™; deutetrabazine) for Huntington's chorea.

$GABA_A$ alpha-5 negative allosteric modulators are shown to act as rapid antidepressants in several mouse models of depression. A use patent was subsequently filed for the use of $GABA_A$ alpha5 NAMs as antidepressant agents. In order to design a drug composition for fast-acting treatment of depression and related conditions, (1,1-Dioxidothiomorpholino)(6-((3-(4-fluorophenyl)-5-methylisoxazol-4-yl)methoxy)pyridin-3-yl)methanone (known as RG-1662), a $GABA_A$ alpha5-selective NAM which was shown to be safe (but not efficacious) in phase II clinical trials as a nootropic, was used as a lead.

In one embodiment, the present invention relates to a composition and methods of using the composition for treating and/or ameliorating depression and/or suicidality in a human subject, and other depression-related disorders comprising administering to the subject a therapeutically effective amount of a deuterated negative allosteric modulator of $GABA_A Rs$ containing alpha5 subunits. In a more preferred embodiment, the modulator is a version of RG-1662), a $GABA_{A5}R$ negative allosteric modulator (NAM) that has been previously shown to be safe in phase II clinical trials, which has been modified by substitution of deuterium for hydrogen atoms at one or more specific sites that are sites of hydrolysis in the liver in order to prolong its half-life in the human body.)

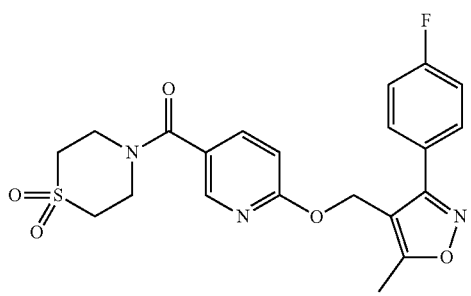

(1,1-Dioxidothiomorpholino)6-((3-(4-fluorophenyl)-
5-methylisoxazol-4-yl)methoxy) pyridin-3-yl)metha-
none

B. Compounds

Selective negative allosteric modulators for $GABA_AR$s containing alpha5 subunits (such as ethyl (13aS)-7-methoxy-9-oxo-11,12,13,13 a-tetrahydro-9H-imidazo[1,5-a]pyrrolo[2,1-c][1,4]benzodiazepine-1-carboxylate (L-655,708), 3-bromo-10-(difluoromethyl)-9H-benzo[f]imidazol[1,5-a][1,4]diazepine (RO4938581), N-benzyl-6-ethoxy-4-oxo-1H-1,5-naphthyridine-3-carboxamide (CP-457,920), 3-tert-Butyl-7-(5-methylisoxazol-3-yl)-2-(1-methyl-1H-1,2,4-triazol-5-ylmethoxy)pyrazolo(1,5-d)(1,2,4)triazine (MRK-016), (1,1-Dioxidothiomorpholino)(6-((3-(4-fluorophenyl)-5-methylisoxazol-4-yl)methoxy)pyridin-3-yl)methanone (RG-1662) can be modified by substituting deuterium ions for hydrogen ions at positions in the molecules that are substrates for hydrolysis by degradative liver enzymes. This modification slows down the compounds' rate of hydrolysis and catabolism in the body. This prolongs bioavailability of the compounds regardless of delivery route and increases their clinical utility as fast acting antidepressants.

Existing alpha5 subunit selective negative allosteric modulators of $GABA_AR$ are not optimally effective because their pharmacokinetic profiles are too fast (short half-life) due to rapid hydrolysis by catalytic liver enzymes, reducing bioavailability at the critical receptors needed to provide therapeutic relief. By introducing a deuterium at one or more sites of metabolic hydrolysis, the rate of catabolism is slowed, thereby increasing bioavailability and therapeutic efficacy, and reducing the need for frequent dosing of the drug and use of fewer doses, thereby lowering potential side effects and improving compliance.

The compounds according to the invention therefore preferably are deuterated. The deuterium content at any particular hydrogen atom in the compounds can range from no deuterium (or the natural abundance of deuterium), up to about 95% deuterium or more. Preferably, the hydrogen atoms that are the sites of hydrolysis in liver metabolism are enriched in deuterium. These sites were first identified in in vitro assays using cultured hepatocytes so as to be able to specifically direct their chemical substitution. When this deuteration procedure has been performed on RG-1662, this compound is referred to as NCGC-43 herein.

Preferred compounds are derived from GR-1662 and are selected from the group consisting of (3-(4-fluophenyl)-5-(methyl-d3)isoxazol-4-yl)methanol; 6-((3-(4-fluorophenyl)-5-(methyl-d3)isoxazol-4yl-methoxy)nicotinonitrile; 6-((3-(4-fluorophenyl)-5-(methyl-d3)isoxazol-4-yemethoxy) nicotinic acid; and (1,1-dioxidothiomorpholino)(6-((3-(4-fluorophenyl)-5-(methyl-d3)isoxazol-4-yl)methoxy) pyridine-3-yl)methadone (NCGC-43). In preferred embodiments of the invention, the deuterated alpha5 subunit-selective GABA-NAM compound is synthesized using the reaction/synthesis methods described in Example 1, and the deuterated compound characterized using NMR.

Compounds according to the invention include the GABA-NAM compounds:

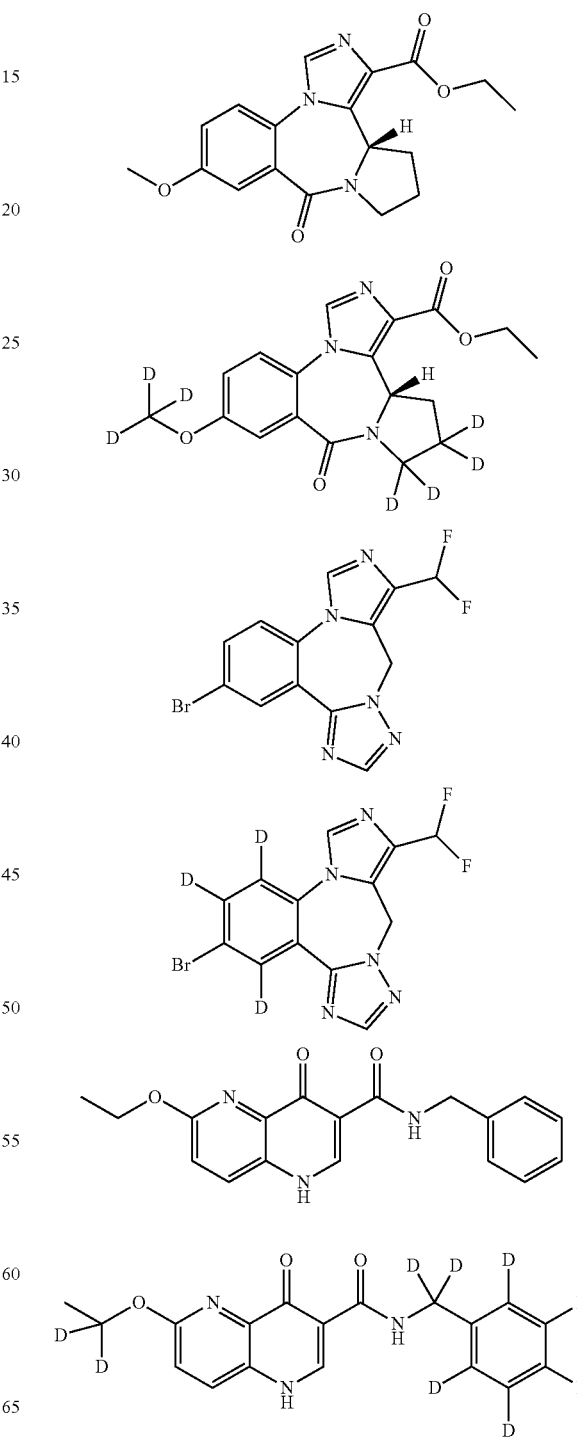

-continued

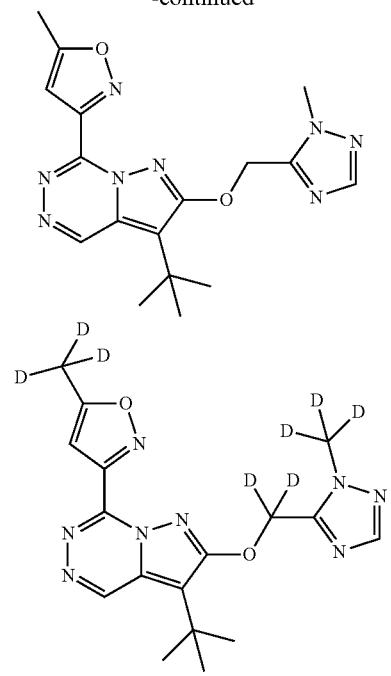

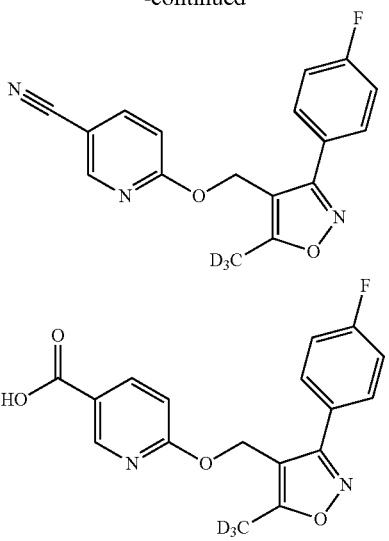

The preferred compound is

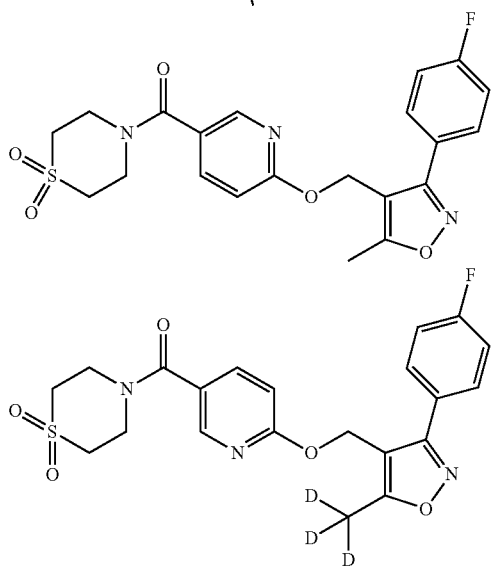

which preferably are deuterated, and most preferably are deuterated at the location where liver metabolism occurs in the compound.

In addition, the invention includes the intermediate compounds

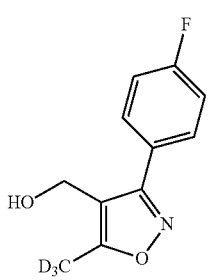

The compounds of the invention include the base, and any pharmaceutically acceptable hydrate, solvate, acid or salt thereof, and can be amorphous or in any crystalline form, or as an oil or wax. Any pharmaceutically acceptable salt can be used, as may be convenient. Generally, these salts are derived from pharmaceutically and biologically acceptable inorganic or organic acids and bases or metals. Examples of such salts include, but are not limited to: acetate, adipate, alginate, ammonium, aspartate, benzoate, benzenesulfonate (besylate), bicarbonate, bisulfate, butyrate, citrate, camphorate, camphorsulfonate, carbonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, magnesium, maleate, malonate, methanesulfonate (mesylate), 2-naphthalenesulfonate, nicotinate, nitrate, oxalate, palmoate, pectinate, persulfate, 3-phenylpropionate, phosphate, picrate, pivalate, potassium, propionate, salicylate, sodium, succinate, sulfate, tartrate, thiocyanate, toluenesulfonate (tosylate) and undecanoate salts.

The compounds also include any or all stereochemical forms of the therapeutic agents (i.e., the R and/or S configurations for each asymmetric center). Therefore, single enantiomers, racemic mixtures, and diastereomers of the therapeutic agents are within the scope of the invention. Also within the scope of the invention are steric isomers and positional isomers of the therapeutic agents. The therapeutic agents of some embodiments are also meant to include compounds which differ only in the presence of one or more isotopically enriched atoms. For example, therapeutic agents in which one or more atom is replaced by, for example, deuterium, tritium, $^{13}C$, $^{14}C$ (or any isotopic labels as commonly used in the art such as phosphorus, calcium, iodine, chlorine, bromine, or any other convenient element for isotopic labeling) are within the scope of this invention.

C. Compositions

In a preferred method embodiments, the compounds described herein are formulated and are administered as a pharmaceutical composition that includes a pharmaceutically acceptable carrier and one or more pharmaceutical agent, including one or more of the inventive compounds described herein, and including one or more of the inventive compounds described herein with an additional agent, such as an anticancer drug of another class. A pharmaceutically acceptable carrier refers to any convenient compound or group of compounds that is not toxic and that does not destroy or significantly diminish the pharmacological activity of the therapeutic agent with which it is formulated. Such pharmaceutically acceptable carriers or vehicles encompass any of the standard pharmaceutically accepted solid, liquid, or gaseous carriers known in the art, such as those discussed in the art.

A suitable carrier depends on the route of administration contemplated for the pharmaceutical composition. Routes of administration are determined by the person of skill according to convenience, the health and condition of the subject to be treated, and the location and stage of the condition to be treated.

Such routes can be any route which the practitioner deems to be most effective or convenient using considerations such as the patient, the patient's general condition, and the specific condition to be treated. For example, routes of administration can include, but are not limited to local and parenteral, including oral, topical, transdermal, buccal, sublingual, transmucosal, wound covering, inhalation, insufflation, rectal, vaginal, nasal, wound covering, intravenous injection, intramuscular injection, intra-arterial injection, intrathecal injection, subcutaneous injection, intradermal injection, intraperitoneal injection, direct local injection, and the like. The administration can be given by transfusion or infusion, and can be administered by an implant, an implanted pump, or an external pump, or any device known in the art.

Therefore, the forms which the pharmaceutical composition can take will include, but are not limited to: tablets, capsules, caplets, lozenges, dragees, pills, granules, oral solutions, powders for dilution, powders for inhalation, vapors, gases, sterile solutions or other liquids for injection or infusion, transdermal patches, buccal patches, inserts and implants, rectal suppositories, vaginal suppositories, creams, lotions, oils, ointments, topical coverings (e.g., wound coverings and bandages), suspensions, emulsions, lipid vesicles, and the like.

Any pharmaceutically acceptable carrier is contemplated for use with the invention, such as the carriers and excipients known in the art. Carriers can include, for example, starch (e.g., corn starch, potato starch, rice starch), celluloses (e.g., microcrystalline cellulose, methylcellulose, and the like), sugars (e.g., lactose, sucrose, glucose, fructose, and the like), clays, minerals (e.g., talc, and the like), gums, flavorings, odorants and fragrances, preservatives, colorings, taste-masking agents, sweeteners, gels, waxes, lipids (e.g., lipid vesicles or nanoparticles), oils, polyethylene glycols, glycerine, propylene glycol, solvents (e.g., water or pharmaceutically acceptable organic solvents), saline solutions (e.g., saline solutions, electrolyte solutions, lactated saline solutions, and the like), emulsifiers, suspending agents, wetting agents, fillers, adjuvants, dispersants, binders, pH adjusters and buffers, antibacterial agents (e.g., benzyl alcohol, methyl parabens, and the like), antioxidants (e.g., ascorbic acid, sodium bisulfite, and the like), chelating agents (e.g., EDTA and the like), glidants (e.g., colloidal silicon dioxide), and lubricants (e.g., magnesium stearate and the like). The compounds or pharmaceutical compositions containing the compounds can be provided in containers such as blister packs, ampoules, bottles, pre-filled syringes, and the like. Extended and sustained release compositions also are contemplated for use with and in the inventive embodiments. Thus, suitable carriers can include any of the known ingredients to achieve a delayed release, extended release or sustained release of the active components. Preferably, the pharmaceutical compositions comprise a therapeutically effective amount.

D. Doses

According to an embodiment of the invention, deuterated alpha5-selective GABA-NAMs, such as NCGC-43 are administered to a human subject in a therapeutically effective amount by any convenient route of administration. The dose of the inventive compound is administered to the subject at convenient intervals such as every 0.5, 1, 2, 3 or more days, weekly, or at any convenient interval, in repetitive dosing regimens. The compound can be administered alone as a monotherapy, or in combination with one or more other therapies, either in the same dosage form or in separate dosage forms, provided at the same time or at different times, in single doses or in a repetitive dosing regimen.

Treatment regimens include a single administration or a course of administrations lasting two or more days, including a week, two weeks, several weeks, a month, 30 days, 60 days, 90 days, several months, six months, a year, or more, including administration for the remainder of the subject's life. The regimen can include multiple doses per day, one dose per day or per week, for example, or a long infusion administration lasting for an hour, multiple hours, a full day, or longer.

Dosage amounts per administration include any amount determined by the practitioner, and will depend on the size of the subject to be treated, the state of the health of the subject, the route of administration, the condition to be treated or prevented, and the like. In general, it is contemplated that for the majority of subjects, a dose in the range of about 0.01 mg/kg to about 100 mg/kg is suitable, preferably about 0.1 mg/kg to about 50 mg/kg, more preferably about 0.1 mg/kg to about 10 mg/kg, and most preferably about 0.2 mg/kg to about 5 mg/kg are useful. This dose can be administered weekly, daily, or multiple times per day. A dose of about 0.1 mg, 0.2 mg, 0.25 mg, 0.5 mg, 1 mg, 5 mg, 10 mg, 20 mg, 40 mg, 80 mg, 100 mg, 250 mg, 500 mg, or 1000 mg can be administered.

Preferably, a therapeutically effective dose results in the presence of the deuterated compounds in the cerebrospinal fluid of the subject at a concentration sufficient to bind to 10 to 75% of all $GABA_AR$ in order to reduce $GABA_AR$ function by at least about 10 to 75%. In addition, preferred deuterated compositions have a long half-life when therapeutically administered to a mammal such as a human subject, including analogs and derivatives of the deuterated RG-1662 compounds which have other deuterium atom substitutions in order to yield enhanced bioavailability and increased half-life when administered to a human subject.

In certain embodiments, the inventive methods involve administration of a therapeutically effective amount of deuterated alpha5 subunit-selective GABA-NAMs in combination (sequentially or concomitantly) with another antidepressant drug. The antidepressant drugs can include, for example, one or more of a monoamine oxidase inhibitor, a selective serotonin reuptake inhibitor, a serotonin-norepinephrine reuptake inhibitor, a triple reuptake inhibitor, a CNS acetylcholine function modulator, a stimulant, an antiglucocorticoid, an NMDA-type glutamate receptor antagonist, a tricyclic antidepressant, a drug used to reduce craving and withdrawal in substance abuse disorder or alcoholism, and any combination thereof.

E. Methods $GABA_{A5}$-NAM compounds, of which RG-1662 is a member, have potential utility in treating psychiatric and neurological conditions such as Down's Syndrome, bipolar disorder, pathological anxiety, and autism spectrum disorders. Here, the invention relates to methods for treating, preventing, or ameliorating at least one symptom in an individual suffering from a depression related disorder as defined above.

The subjects contemplated as "in need" of the inventive methods refers to any animal, preferably a mammal, and most preferably a human patient suffering from a depression-related disorder, including any disorder causing, related to or defined by depression and any disorder or condition having depressive symptoms. As used herein, this term also includes cognitive, memory and psychotic disorders. Depressive disorders include, but are not limited to general depression, major depressive disorder (clinical depression), dysthymia, suicidality, unipolar depression, bipolar depression, psychotic depression, atypical depression, seasonal affective disorder, premenstrual dysphoric disorder, endogenous depression, catatonic depression, post-traumatic stress disorder, postpartum depression, posttraumatic stress disorder, and any combination thereof. Other disorders and conditions included in the definition of depression-related disorders are anxiety-related disorders; anhedonia; attention-related disorders; psychosis-related disorders; personality disorders; sleep disorders; eating disorders; cognitive impairment (including that which follows traumatic brain injury (TBI) or non-TBI-related cognitive impairment; memory impairment; disorders of learning; neuropathic pain; chronic muscle or bone pain; diabetic neuropathy; generalized attack of muscular weakness; recurring sleep episodes during the day; migraine; addiction; or a combination thereof. Other disorders and conditions included in the definition of depression-related disorders are those in with these symptoms occur as a secondary consequence of some other primary medical condition, such as a tumor, substance abuse disorder, alcoholism. Such subjects are treated by administration of the deuterated RG-1662 compound NCGC-43 or composition in an amount of about 0.1 mg to about 1000 mg preferably administered about once per day, week, month, or on an as needed basis. The preferred routes of administration are oral, topical, transdermal, buccal, sublingual, transmucosal, wound covering, inhalation, insufflation, rectal, vaginal, nasal, wound covering, intravenous injection, intramuscular injection, intra-arterial injection, intrathecal injection, subcutaneous injection, intradermal injection, intraperitoneal injection, direct local injection, and the like. The administration can be given by transfusion or infusion, and can be administered by an implant, an implanted pump, or an external pump, or any device known in the art.

4. Examples

This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Although any methods and materials similar or equivalent to those described herein can be used in the practice or testing of embodiments of the present invention, the preferred methods, devices, and materials are now described. All publications mentioned herein, are incorporated by reference in their entirety; nothing herein is to be construed as an admission that the invention is not entitled to antedate such disclosure by virtue of prior invention.

Example 1: Chemical Synthetic Methods

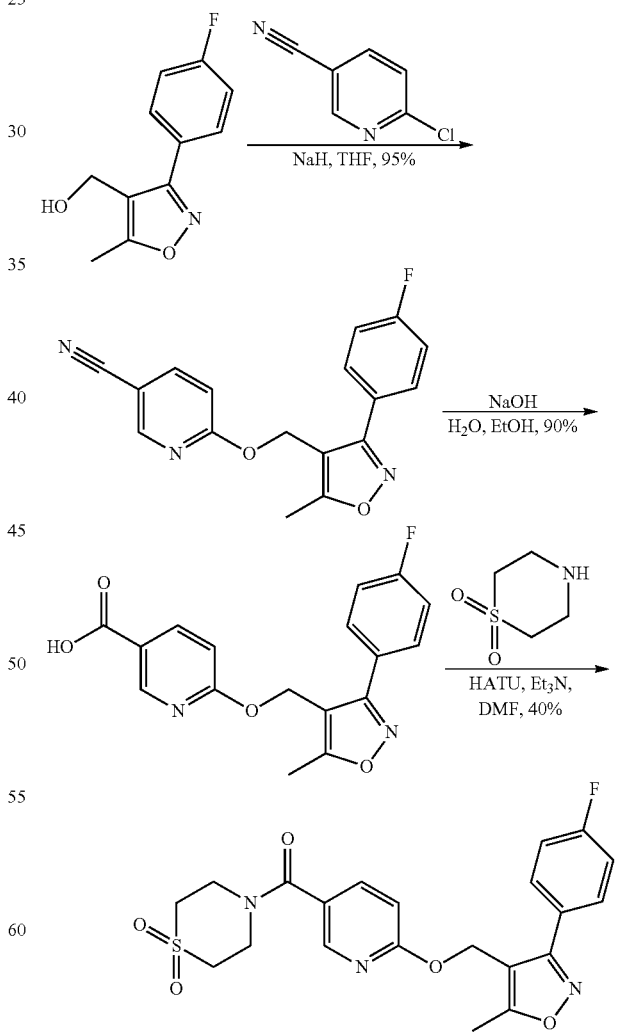

NCGC00508843 was synthesized from (3-(4-fluorophenyl)-5-methylisoxazol-4-yl)methanol as follows. Treatment of (3-(4-fluorophenyl)-5-methylisoxazol-4-yl)methanol with sodium deuteroxide in a mixture of deuterium oxide and deuterated methanol at elevated temperature yielded (3-(4-fluorophenyl)-5-(methyl-d3)isoxazol-4-yl)methanol. This was followed by nucleophilic aromatic substitution with 6-chloronicotinonitrile to yield 6-((3-(4-fluorophenyl)-5-(methyl-d3)isoxazol-4-yl)methoxy)nicotinonitrile. Hydrolysis of the nitrile to the acid in deuterated solvents also increased the deuterium incorporation to 95%. Finally, amide coupling with thiomorpholine 1,1-dioxide yielded NCGC-43.

The deuterated compounds were synthesized from RG-1662 to produce (1,1-dioxidothiomorpholino)(6-((3-(4-fluorophenyl)-5-(methyl-d3)isoxazol-4-yl)methoxy)pyridin-3-yl)methanone (NCGC00508843; NCGC-43) in four steps from commercial materials, with a 33% overall yield. Deuterium incorporation was measured By $^1$H NMR to be 95%.

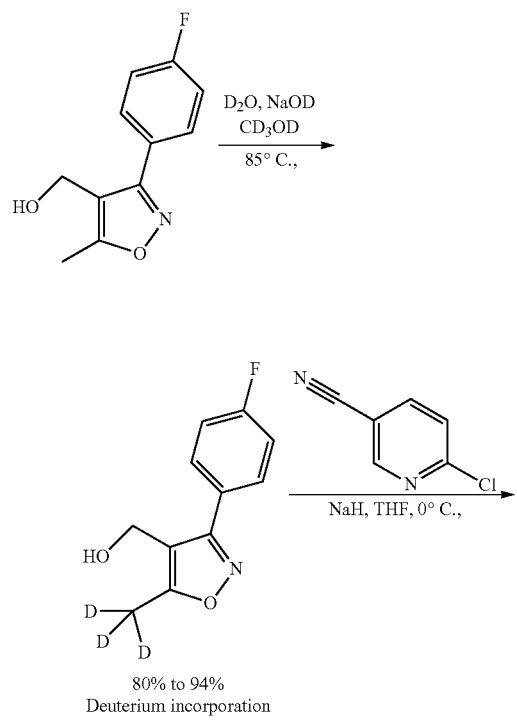

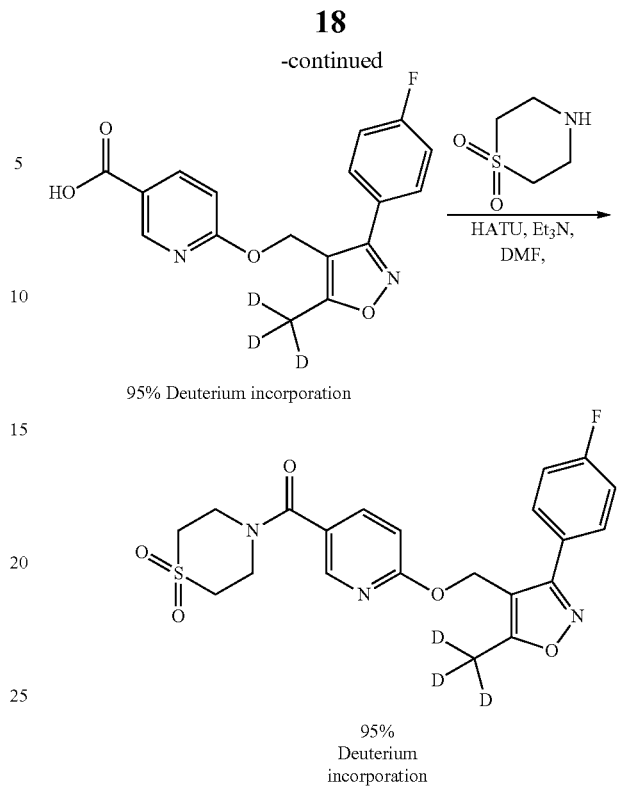

Synthesis of (3-(4-fluorophenyl)-5-(methyl-d3)isoxazol-4-yl)methanol was accomplished as follows. (3-(4-Fluorophenyl)-5-(methyl-d3)isoxazol-4-yl)methanol (500 mg, 2.4 mmol) was placed in a microwave vial with a stir bar. To this was added 2.0 mL of deuterium oxide, 8.0 ml of CD$_3$OD and 1.0 ml of 30% NaOD in in D$_2$O. The vial was sealed and heated to 85° C. for two hours with microwave irradiation. The vial then was cooled, and quenched by addition to aqueous ammonium chloride. The compound was extracted into ethyl acetate, and the solvent was removed by rotary evaporation to give the title product as a white solid in 99% yield (504 mg) without further purification. $^1$H NMR analysis indicated about 80% deuterium incorporation. $^1$H NMR (400 MHz, cdcl$_3$) δ 7.91-7.68 (m, 2H), 7.18-6.98 (m, 2H), 4.48 (s, 2H), 2.41-2.36 (m, 0.6H, 80% deuterium incorporation). $^{13}$C NMR (101 MHz, cdcl$_3$) δ 168.7, 163.7 (d, J$_{c-F}$=251.5 Hz, 1C) 161.7, 130.4, 130.3, 125.2, 116.1, 115.9, 113.0, 53.6, 10.7 (m, C-D splitting). MS: Expected: 211.2 (M+H). Observed: 211.1.

6-((3-(4-Fluorophenyl)-5-(methyl-d3)isoxazol-4-yl)methoxy)nicotinonitrile was synthesized as follows. Sodium hydride (120 mg, 2.9 mmol, 60% dispersion in mineral oil)

was added to a solution of (3-(4-fluorophenyl)-5-(methyl-d3)isoxazol-4-yl)methanol (504 mg, 2.4 mmol) in tetrahydrofuran (THF) (5.0 mL) at 0° C. Then, a solution of 6-chloroniconinonitrile (400 mg, 2.9 mmol) in THF (5.0 mL) was added via syringe. The reaction was allowed to warm to room temperature and stirred for two hours. It was then quenched by addition to aqueous sodium bicarbonate. The reaction was extracted into ethyl acetate, and the solvent removed by rotary evaporation. Purification by silica gel chromatography (0% to 100% ethyl acetate in hexanes) gave the title product as a white solid in 75% yield (560 mg). Deuterium incorporation was maintained at about 80%. $^1$H NMR (400 MHz, cdcl$_3$) δ 8.47 (dd, J=2.3, 0.8 Hz, $^1$H), 7.81 (dd, J=8.7, 2.3 Hz, $^1$H), 7.77-7.66 (m, 2H), 7.19-7.05 (m, 2H), 6.84 (dd, J=8.7, 0.8 Hz, $^1$H), 5.29 (s, 2H), 2.57-2.51 (m, 0.6H, 80% deuterium incorporation). $^{13}$C NMR (101 MHz, cdcl$_3$) δ 170.3, 164.8, 163.8 (d, $J_{c-F}$=250.5 Hz, 1C) 162.0, 151.7, 141.5, 130.3, 130.2, 125.2 (d, Jc_p=3.0 Hz, 1C), 117.0, 116.2, 116.0, 112.2, 109.1, 103.3, 57.8, 11.2 (m, C-D splitting). MS: Expected: 313.3 (M+H). Observed: 313.1.

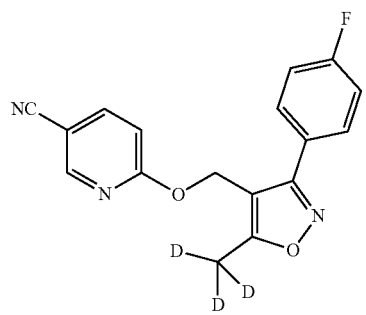 [SMILES: [2H]C([2H])([2H])c1onc(-c2ccc(F)cc2)c1COc1ccc(C#N)cn1]

6-((3-(4-Fluorophenyl)-5-(methyl-d3)isoxazol-4-yl) methoxy)nicotinic acid was synthesized as follows. Deuterium oxide (5.0 ml) and sodium deuteroxide (2.5 g, 18 mmol, 30% weight in D$_2$O) was added to a vial containing a solution of 6-((3-(4-(4-fluorophenyl)-5-(methyl-d3)isoxazol-4-yl)methoxy)nicotinonitrile (560 mg, 1.8 mmol)) in d4-methanol (7.0 mL). The vial was sealed, and the reaction was heated to 55° C. and stirred for 16 hours. The vial then was cooled and quenched with aqueous hydrochloric acid. The pH was adjusted to 2 and the reaction was extracted with ethyl acetate to give the crude product (560 mg), which was used without further purification. Deuterium incorporation increased to about 95% incorporation.

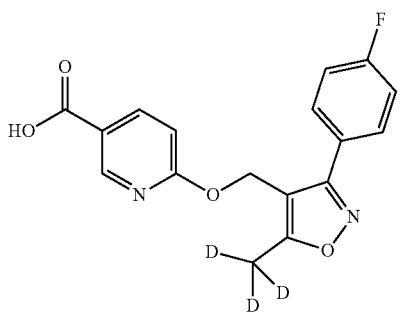 [SMILES: [2H]C([2H])([2H])c1onc(-c2ccc(F)cc2)c1COc1ccc(C(=O)O)cn1]

(1,1-dioxidothiomorpholino)(6-((3-(4-fluorophenyl)-5-(methyl-d3)isoxazol-4-yl)methoxy)pyridin-3-yl)methanone (NCGC00508843) was synthesized as follows. Crude 6-((3-(4-fluorophenyl)-5-(methyl-d3)isoxazol-4-yl)methoxy) nicotinic acid (560 mg, 1.7 mol) was dissolved in dimethyl formamide (DMF) (3.0 mL). To this was added thiomorpholine, 1,1-dioxide hydrochloride (350 mg, 2.0 mmol), followed by hexafluorophosphate azabenzotriazole tetramethyl uronium (HATU) (770 mg, 2.0 mmol) and trimethylamine (350 mg, 3.4 mmol). The reaction was stirred for 2 hours. It was then poured into water, and extracted with diethyl ether (3×). The organic extracts were combined and the solvent removed by rotary evaporation. Purification by silica gel chromatography (0% to 100% ethyl acetate in hexanes) gave the desired product. The solvent was removed, the compound was redissolved in ethanol, and the ethanol was removed by rotary evaporation to give the desired product as a white solid, in 45% yield (340 mg). Deuterium incorporation was measured to be 95% by $^1$H NMR. $^1$H NMR (400 MHz, cdcl$_3$) δ 8.28 (dt, J=2.4, 0.8 Hz, $^1$H), 7.80-7.72 (m, 2H), 7.70 (ddd, J=8.5, 2.4, 0.7 Hz, $^1$H), 7.18-7.08 (m, 2H), 6.82 (dt, J=8.6, 0.8 Hz, $^1$H), 5.26 (s, 2H), 4.24-3.95 (m, 4H), 3.12-3.02 (m, 4H), 2.55-2.50 (m, 0.05H (95% deuterium)). $^{13}$C NMR (101 MHz, cd$_3$od) δ 171.8, 170.7, 165.4, 165.1(d, $J_{c-F}$=247 Hz, 1C) 163.3, 147.5, 139.8, 131.6, 131.5, 125.6, 117.0, 116.8, 112.1, 111.8, 111.0, 58.1, 52.7, 38.9. MS: Expected: 449.5 (M+H). Observed: 449.1. MP: 132.3° C.

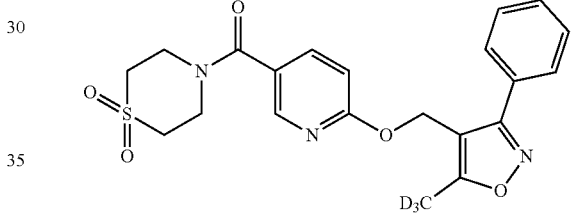

See FIG. 1 for NMR spectra of intermediary compounds, as labelled. When the final compound is not stable as the HCl salt, another salt can be used or the compound can be formulated as the free base.

Figure 2:
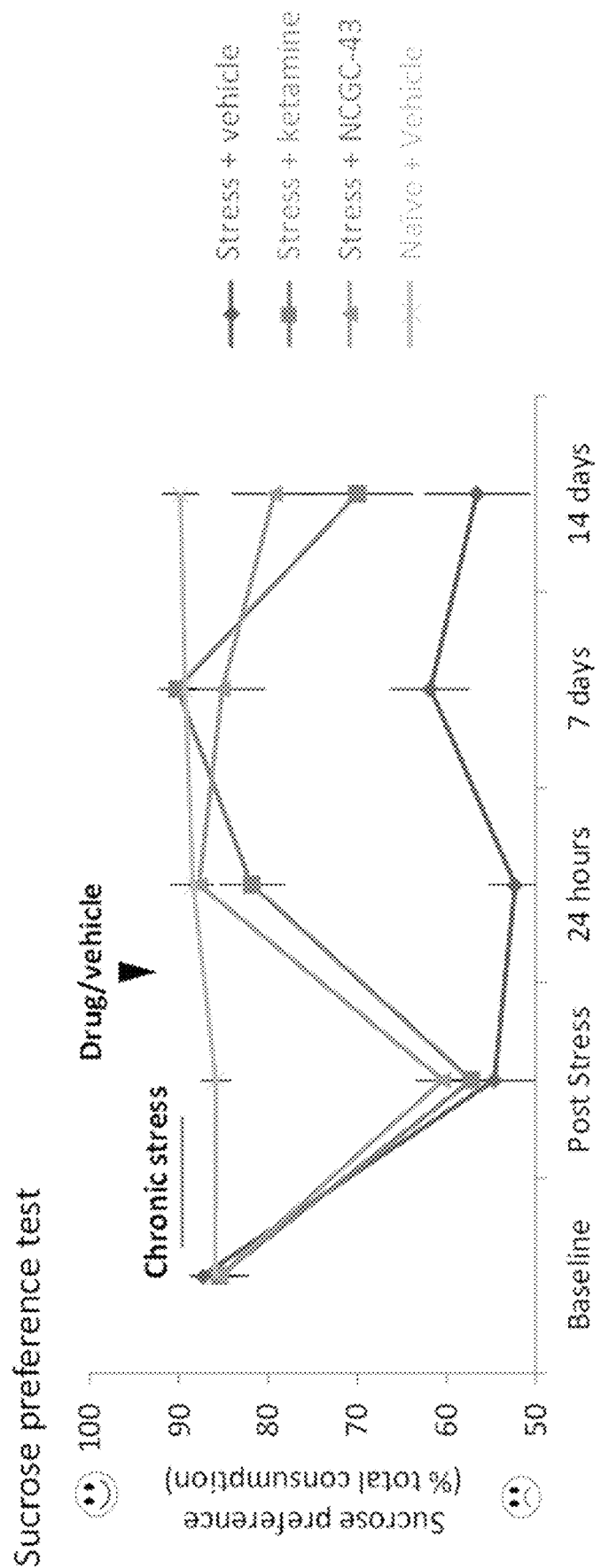
FIG. 2 is a graph showing results for a sucrose preference test under the indicated conditions.

Example 2. Preclinical Studies of Antidepressant Actions and Lack of Anxiogenic Actions FIG. 2 shows a comparison of NCGC-43 and ketamine in the sucrose preference test demonstrating the ketamine-like fast and persistent antidepressant effect of NCGC-43. In the sucrose preference test, rats were given an overnight two bottle choice task (in which the sucrose solution consumption is shown as a percentage of the total solution consumed) before commencing stress (baseline), immediately after 14 days of chronic multimodal stress, and 24 hours, 7 days, and 14 days after an injection of NCGC-43 (3 mg/kg, gray), ketamine (20 mg/kg, orange), or vehicle (DMSO solution, blue), all while continuing with daily chronic multimodal stress. A control group received neither stress nor drug (yellow). Chronic stress decreased sucrose preference, a sign of anhedonia, whereas a single injection of ketamine or NCGC-43 restored sucrose preference in a rapid (within 24 hours) and persistent (up to 14 days) manner.

The effects of NCGC-43 were comparable to ketamine, which is known to produce rapid and persistent antidepressant effects in humans.

Figure 3:
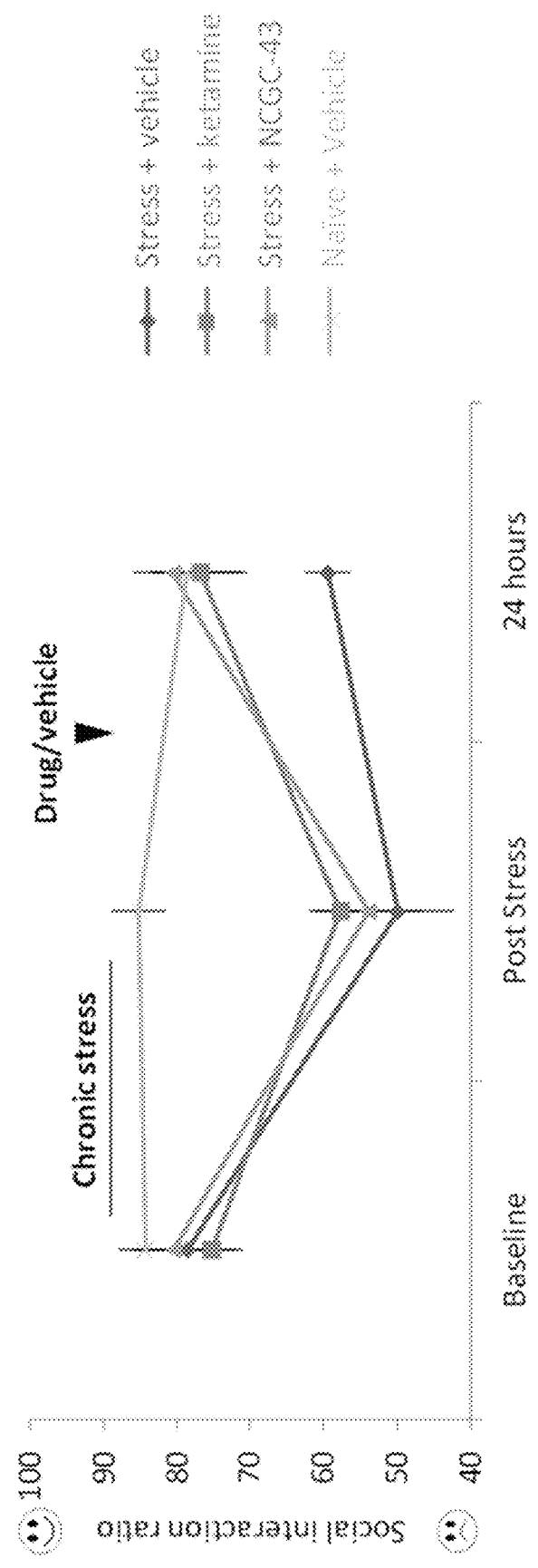
FIG. 3 is a graph showing results for a social interaction test under the indicated conditions.
Figure 4C:
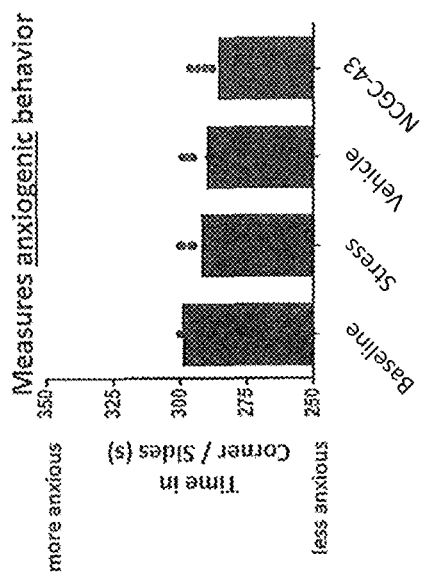
FIG. 4B, FIG. 4C, FIG. 4D, and FIG. 4E are bar graphs showing the results of the open field test as indicated.
Figure 4A:
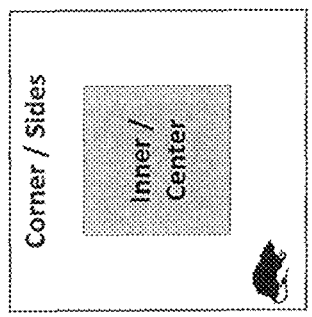
FIG. 4A is a schematic of the open field test.
Figure 4B:
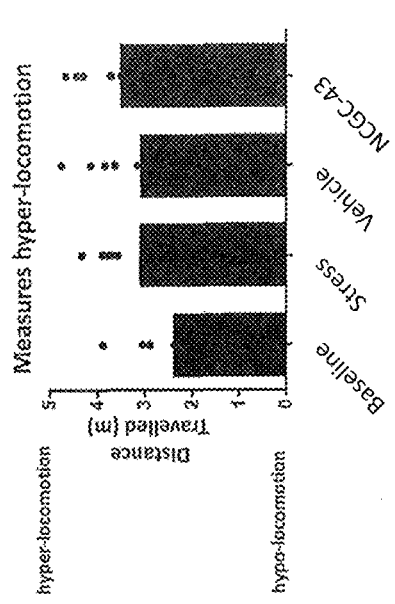
Figure 4E:
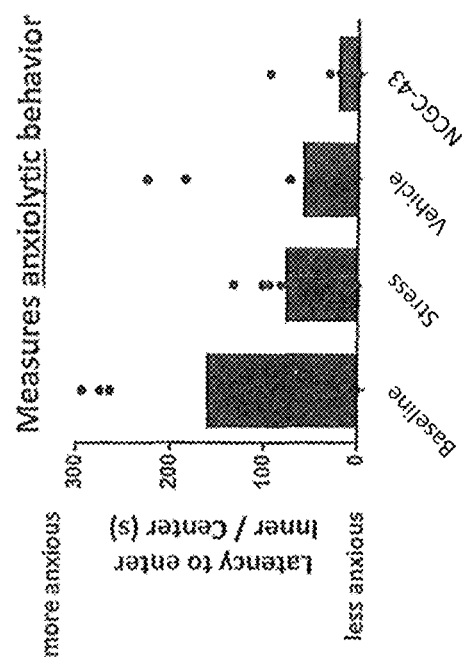
Figure 4D:
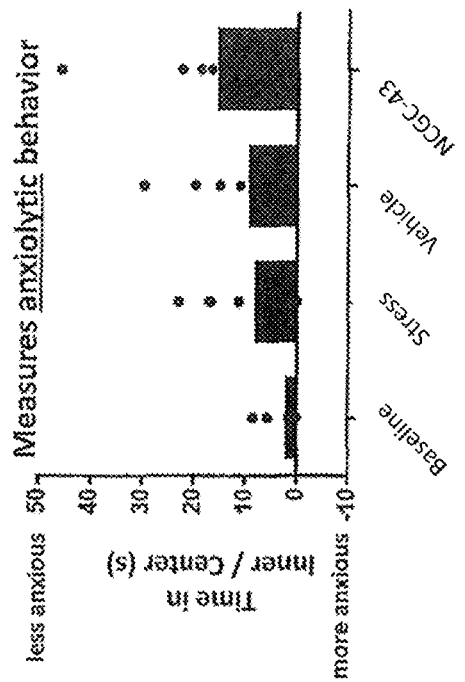

FIG. 3 shows a comparison of NCGC-43 and ketamine in the social interaction test demonstrating the ketamine-like fast and persistent antidepressant effect of NCGC-43. In the social interaction test, rats were given a choice between spending time in a chamber with a novel caged juvenile rat and a chamber with an empty cage. In the social interaction test, rats were given a choice between spending time in a chamber with a novel caged juvenile rat and a chamber with an empty cage before commencing stress (baseline), immediately after 14 days of chronic multimodal stress, and 24 hours after an injection of NCGC-43 (3 mg/kg, gray), ketamine (20 mg/kg, orange), or vehicle (DMSO solution, blue). Social interaction computed as percent time spent with the novel animal. A control group received neither stress nor drug (yellow). Chronic stress decreased social interactions, a sign of anhedonia, whereas a single injection of ketamine or NCGC-43 restored their preference for interacting with a novel animal.

FIG. 4 shows the effects of NCGC-43 in the open field test. FIG. 4A is a schematic of the open field test. FIG. 4B shows that neither chronic stress nor injection of NCGC-43 or vehicle had any significant effects on overall locomotor activity. FIG. 4C shows that neither chronic stress nor injection of NCGC-43 or vehicle had any significant effects on the time the animal spent in the corners and sides during the testing procedures, consistent with no change in the animals' state of anxiety under any condition. FIG. 4D shows that neither chronic stress nor injection of NCGC-43 or vehicle had any significant effects on the ratio of the time the animal spent in the center of the chamber to the time spent in the corners/sides during the testing procedures, consistent with no change in the animals' state of anxiety under any condition. FIG. 4E shows that neither chronic stress nor injection of vehicle NCGC-43 or vehicle had any significant effects on the latency before the animals first entered the center of the chamber, consistent with no change in the animals' state of anxiety, whereas NCGC-43 mildly decreased the latency, consistent with a modest anxiolytic effect. Behavioral measurements were made before commencing stress (baseline), immediately after 14 days of chronic multimodal stress, and 24 hours after an injection of NCGC-43 (3 mg/kg) or vehicle (DMSO solution).

FIG. 5 shows a comparison of NCGC-43 and ketamine in the elevated plus maze, demonstrating the lack of an anxiolytic response to NCGC-43. In the elevated plus maze, rats were given a choice between spending time in one of two arms of an elevated cross-shaped maze (one arm closed and the other arm open), immediately after 14 days of chronic multimodal stress, and 24 hours after an injection of NCGC-43 (3 mg/kg) or ketamine (20 mg/kg). A control group was unstressed and received a vehicle injection (DMSO). A single injection of ketamine increased the percent of time the rat spent in the closed arm, consistent with an increase in anxiety or fear. Neither stress nor NCGC nor vehicle injection had an effect on time spent in the closed arm, consistent that they did not increase anxiety or fear.

Figures 6A, 6B:
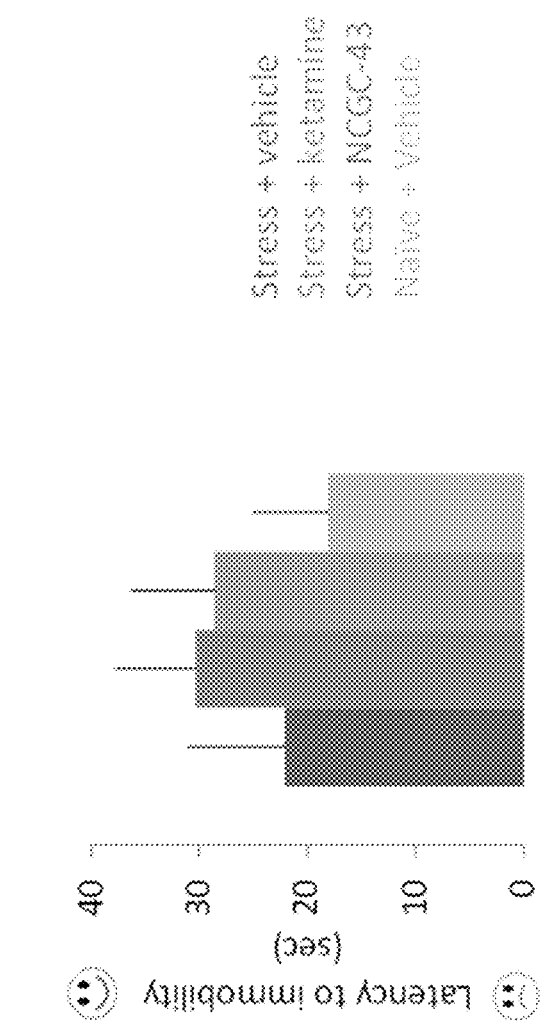
FIG. 6A, FIG. 6B, FIG. 6C, and FIG. 6D are graphs showing results of the forced swim test as indicated (% time immobile (FIG. 6A), latency to immobility (FIG. 6B), time immobile (FIG. 6C) and immobile episodes (FIG. 6D).
Figures 6C, 6D:
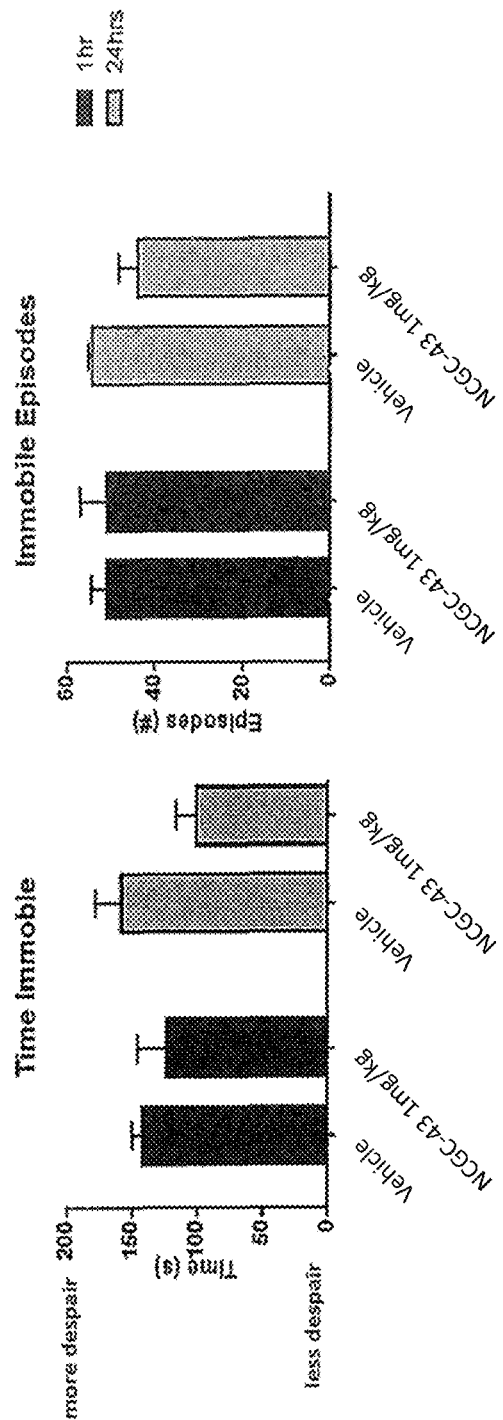

FIG. 6 shows a comparison of NCGC-43 and ketamine in the forced swim test. In the forced swim test, naïve rats and rats subjected to 14 days of chronic multimodal stress are placed in a water-filled tank (for 5 minutes), 1 hour or 24 hours after an injection of NCGC-43 (3 mg/kg), ketamine (20 mg/kg), or vehicle (DMSO solution), and monitored for the time the animals spent immobile (FIG. 6A) and the latency until the animals ceased to struggle and become immobile (FIG. 6B), behavioral responses that are said to be rodent analogs of "behavioral despair." Twenty-four hours after NCGC-43 and ketamine injection, there was a decrease in the time the animals spent immobile (FIG. 6A) and an increase in the latency until the animals ceased to struggle and become immobile (FIG. 6B), compared to stressed animals given vehicle. NCGC-43 and ketamine both exert an antidepressant-like response in this test. Comparison of responses at 1 hour and 24 hours suggest that NCGC-43 exerts rapid and persistent effects similar to those described previously for ketamine (Zanos et al., 2016). See also FIG. 6C and FIG. 6D.

FIG. 7 shows the dose-response relationship of NCGC-43 in the forced swim test. We observed that increasing doses of NCGC-43 delivered intraperitoneally had greater effects on the latency to immobility, regardless of whether it was measured 1 or 24 hours after injection, with significant efficacy at 1 and 3 mg/kg.

Example 3. Metabolic Stability Studies in Hepatocytes

The liver is the major metabolic organ within mammals. Basmisanil is metabolized as follows.

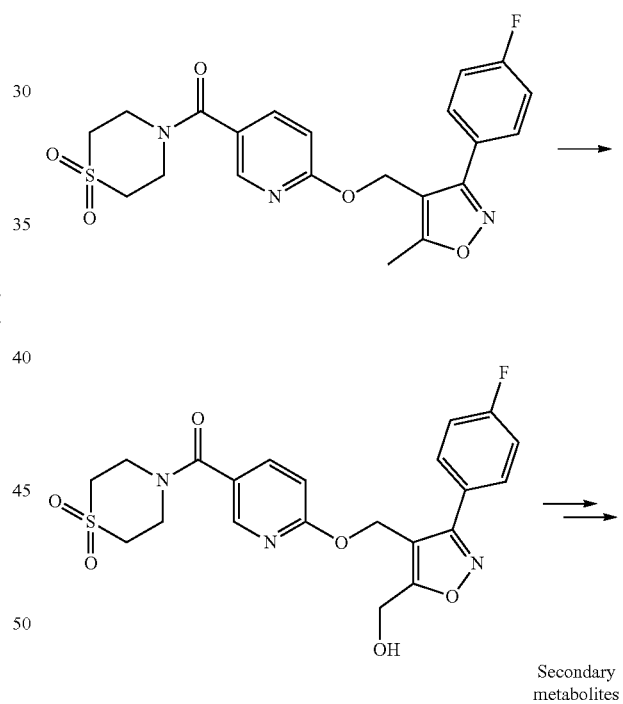

Secondary metabolites

Table 1, below, presents data regarding the half-life of RG-1622 in rat and human liver hepatocytes, in vitro, showing an increase in half-life for the deuterated compounds. Stability improved more in human hepatocytes compared to rat hepatocytes, with variation between the hepatocyte studies. The deuterated RG-1662 compound therefore is more metabolically stable. Longer half-life also allows less frequent dosing. Preferred compounds are more potent and effective, and preferably are deuterated. Deuteration preferably is located at the site of metabolism, since installing deuterium atoms at the site of metabolism more readily increases the half-life of the compound.

TABLE 1

Half-Life of RG-1662 Compounds in Hepatocytes In Vitro.

| Compound Structure | Compound Name | Species | Half-life (hours) | Percentage Remaining at 3 Hours |
|---|---|---|---|---|
| | RG-1662 | rat | 0.6 | 3.3% |
| | RG-1662 | human | 12 | 83.7% |
| | Deuterated RG-1662 (NCGC-43) Deuterated RG-1662 (NCGC-43) | rat human | 0.64 Stable | 3.9% 100% |

In a second study, stability studies showed rapid metabolism in rats, and less rapid metabolism in human hepatocytes, with a rat half-life of 0.33 hours and a human half-life of 6 hours. Metabolite identification studies followed up these assays to confirm the hydrolysis site.

REFERENCES

All references listed below and throughout the specification are hereby incorporated by reference in their entirety.
1. Fischelle, et al., Neuropsychopharmacology, 40:2499-2509, 2015.
2. International Patent Application No. PCT/US2015/023667.
3. Zanos, et al., Nature, 533:481-486, 2016.

The invention claimed is:
1. A deuterated $GABA_{A5}$-NAM compound according to Formula I:

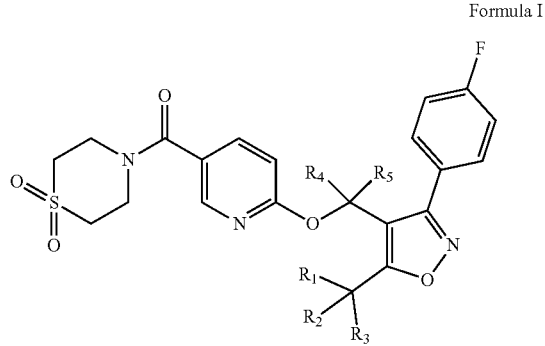

Formula I wherein $R_1$, $R_2$, and $R_3$ each independently are H or D, with the proviso that at least one of $R_1$, $R_2$ and $R_3$ is D, and
wherein $R_4$ and $R_5$ each independently are H or D.

2. The GABAA5-NAM compound: (1,1-dioxidothiomorpholino)(6-((3-(4-fluorophenyl)-5-methylisoxazol-4-yl)methoxy)pyridin-3-yl)methanone (RG-1662); which is deuterated.

3. The deuterated $GABA_{A5}$-NAM compound of claim 1 according to Formula II

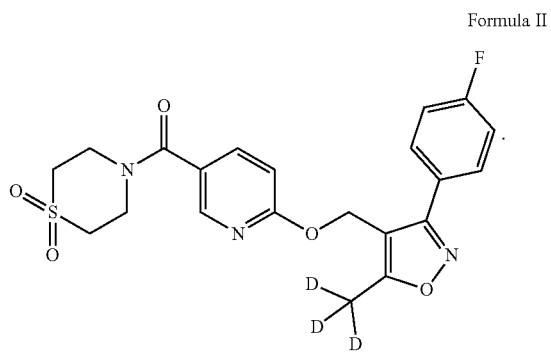 [SMILES: [2H]C([2H])([2H])c1onc(-c2ccc(F)cc2)c1COc1ccc(C(=O)N2CCS(=O)(=O)CC2)cn1]

Formula II

4. A deuterated Basmisanil compound of claim 1 which is synthesized by:
   (a) treating (3-(4-fluorophenyl)-5-methylisoxazol-4-yl) methanol with a base or under basic conditions in the presence of a deuterium donor or followed by a deuterium donor;
   (b) adding the product of step (a) to 6-chloronicotinonitrile or methyl 6-chloronicotinate;
   (c) hydrolyzing the product of step (b) to the carboxylic acid; and (d) amide coupling the product of step (c) with thiomorpholine 1,1-dioxide or a salt there.

5. The compound of claim 3 wherein the deuterium donor is $D_2O$ or $CD_3OD$.

6. A deuterated $GABA_{A5}$-NAM compound of claim 1 which has a longer biological half-life when administered to a mammal than a non-deuterated compound of the same structure.

* * * * *